(12) United States Patent
Shturman

(10) Patent No.: US 9,237,903 B2
(45) Date of Patent: *Jan. 19, 2016

(54) ROTATIONAL ATHERECTOMY DEVICE WITH FLUID INFLATABLE SUPPORT ELEMENTS AND DISTAL PROTECTION CAPABILITY

(71) Applicant: Cardio Flow Inc., Long Lake, MN (US)

(72) Inventor: Leonid Shturman, Nyon (CH)

(73) Assignee: Cardio Flow Inc., Long Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/549,870

(22) Filed: Nov. 21, 2014

(65) Prior Publication Data
US 2015/0094746 A1    Apr. 2, 2015

Related U.S. Application Data

(63) Continuation of application No. 14/189,315, filed on Feb. 25, 2014, now Pat. No. 8,936,589, which is a continuation of application No. 13/783,993, filed on Mar. 4, 2013, now Pat. No. 8,663,195, which is a
(Continued)

(51) Int. Cl.
   *A61B 17/3207* (2006.01)
   *A61B 17/22* (2006.01)
   (Continued)

(52) U.S. Cl.
   CPC ......... *A61B 17/320758* (2013.01); *A61B 17/22* (2013.01); *A61B 17/320725* (2013.01);
   (Continued)

(58) Field of Classification Search
   CPC .............. A61B 2017/22052; A61B 17/32038; A61B 17/3207; A61B 17/22; A61M 25/00

USPC ................................... 604/523; 606/159, 170
   See application file for complete search history.

(56) References Cited

U.S. PATENT DOCUMENTS

| 1,431,416 A | 10/1922 | Parsons et al. |
| 1,916,085 A | 6/1933 | Summers et al. |

(Continued)

FOREIGN PATENT DOCUMENTS

| EP | 0419154 | 3/1991 |
| EP | 0 820 729 | 1/1998 |

(Continued)

OTHER PUBLICATIONS

Declaration of Aleksey Filippov, Apr. 23, 2007, 1 page.
(Continued)

*Primary Examiner* — Victor Nguyen
(74) *Attorney, Agent, or Firm* — Fish & Richardson P.C.

(57) ABSTRACT

A rotational atherectomy device for abrading a stenotic lesion from a vessel of a patient includes a flexible drive shaft (1) which extends towards a distal end of the device, a distal fluid inflatable support element (3, 3") located at a distal end of the drive shaft and an abrasive element (5) mounted to the drive shaft proximal to and spaced away from the distal fluid inflatable support element. Both the abrasive element and the distal fluid inflatable support element are rotatable together with the drive shaft and the drive shaft includes a torque transmitting coil (2) which defines a long lumen of the drive shaft. The distal fluid inflatable support element is formed from a fluid impermeable membrane (9, 9") that crosses a longitudinal axis (x-x) common to the torque transmitting coil and the lumen of the drive shaft at the distal end of the device, thereby preventing pressurized fluid flowing along the lumen of the drive shaft from entering the vessel in the direction of said longitudinal axis so that fluid has to pass through the fluid inflatable support element, inflating said support element and exiting from the device through an outflow opening (66) in the fluid inflatable support element in a direction different from the direction of the longitudinal axis of the coil and the lumen.

5 Claims, 23 Drawing Sheets

Related U.S. Application Data continuation of application No. 13/344,993, filed on Jan. 6, 2012, now Pat. No. 8,388,637, which is a continuation of application No. 12/515,524, filed as application No. PCT/EP2007/062777 on Nov. 23, 2007, now Pat. No. 8,109,955.

(51) Int. Cl.
  *A61B 17/32* (2006.01)
  *A61M 1/00* (2006.01)

(52) U.S. Cl.
  CPC ............. *A61B2017/22052* (2013.01); *A61B 2017/22054* (2013.01); *A61B 2017/22068* (2013.01); *A61B 2017/22071* (2013.01); *A61B 2017/320004* (2013.01); *A61B 2217/005* (2013.01); *A61B 2217/007* (2013.01); *A61M 1/0084* (2013.01)

(56) References Cited

U.S. PATENT DOCUMENTS

| | | | |
|---|---|---|---|
| 4,445,509 A | 5/1984 | Auth | |
| 4,445,892 A * | 5/1984 | Hussein et al. | 604/101.05 |
| 4,646,736 A | 3/1987 | Auth | |
| 4,870,953 A | 10/1989 | DonMicheal et al. | |
| 4,931,635 A | 6/1990 | Toyama | |
| 4,990,134 A | 2/1991 | Auth | |
| 5,100,425 A | 3/1992 | Fischell et al. | |
| 5,217,474 A | 6/1993 | Zacca et al. | |
| 5,242,460 A * | 9/1993 | Klein et al. | 606/159 |
| 5,250,060 A | 10/1993 | Carbo et al. | |
| 5,273,526 A | 12/1993 | Dance | |
| 5,308,354 A | 5/1994 | Zacca et al. | |
| 5,312,427 A | 5/1994 | Shturman | |
| 5,314,407 A | 5/1994 | Auth et al. | |
| 5,314,438 A | 5/1994 | Shturman | |
| 5,342,292 A | 8/1994 | Nita et al. | |
| 5,361,285 A | 11/1994 | Formanek et al. | |
| 5,370,653 A | 12/1994 | Cragg | |
| 5,458,575 A | 10/1995 | Wang | |
| 5,584,843 A | 12/1996 | Wulfman et al. | |
| 5,681,336 A | 10/1997 | Clement et al. | |
| 5,730,717 A | 3/1998 | Gelbfish | |
| 5,843,103 A | 12/1998 | Wulfman | |
| 5,868,708 A | 2/1999 | Hart et al. | |
| 6,010,533 A | 1/2000 | Pope et al. | |
| 6,096,054 A | 8/2000 | Wyzgala et al. | |
| 6,132,444 A | 10/2000 | Shturman | |
| 6,135,982 A | 10/2000 | Campbell | |
| 6,146,395 A | 11/2000 | Kanz et al. | |
| 6,152,911 A | 11/2000 | Giannoble | |
| 6,156,048 A | 12/2000 | Wulfman et al. | |
| 6,241,706 B1 | 6/2001 | Leschinsky et al. | |
| 6,270,465 B1 | 8/2001 | Keith et al. | |
| 6,416,526 B1 | 7/2002 | Wyzgala et al. | |
| 6,485,500 B1 | 11/2002 | Kokish et al. | |
| 6,491,660 B2 | 12/2002 | Guo et al. | |
| 6,565,588 B1 | 5/2003 | Clement et al. | |
| 6,685,718 B1 | 2/2004 | Wyzgala et al. | |
| 6,955,661 B1 | 10/2005 | Herweck et al. | |
| 8,109,954 B2 | 2/2012 | Shturman | |
| 8,109,955 B2 | 2/2012 | Shturman | |
| 8,137,369 B2 | 3/2012 | Shturman | |
| 8,142,458 B2 | 3/2012 | Shturman | |
| 8,147,507 B2 | 4/2012 | Shturman | |
| 8,157,825 B2 | 4/2012 | Shturman | |
| 8,388,636 B2 | 3/2013 | Shturman | |
| 8,388,637 B2 | 3/2013 | Shturman | |
| 8,454,638 B2 | 6/2013 | Shturman | |
| 8,465,510 B2 | 6/2013 | Shturman | |
| 8,496,678 B2 | 7/2013 | Shturman | |
| 8,500,764 B2 | 8/2013 | Shturman | |
| 8,500,765 B2 | 8/2013 | Shturman | |
| 8,663,195 B2 | 3/2014 | Shturman | |
| 8,663,260 B2 | 3/2014 | Shturman | |
| 8,663,261 B2 | 3/2014 | Shturman | |
| 8,936,589 B2 * | 1/2015 | Shturman | 604/523 |
| 2002/0007190 A1 | 1/2002 | Wulfman et al. | |
| 2002/0082547 A1 | 6/2002 | Deniega et al. | |
| 2002/0099367 A1 | 7/2002 | Guo et al. | |
| 2002/0138088 A1 | 9/2002 | Nash et al. | |
| 2002/0188276 A1 | 12/2002 | Evans et al. | |
| 2003/0199889 A1 | 10/2003 | Kanz et al. | |
| 2004/0098014 A1 | 5/2004 | Flugelman et al. | |
| 2004/0158270 A1 | 8/2004 | Wyzgala et al. | |
| 2005/0154416 A1 | 7/2005 | Herweck et al. | |
| 2005/0209615 A1 | 9/2005 | Prudnikov et al. | |
| 2005/0240146 A1 | 10/2005 | Nash et al. | |
| 2005/0256461 A1 | 11/2005 | DiFiore et al. | |
| 2008/0097498 A1 | 4/2008 | Shimizu et al. | |
| 2008/0319415 A1 | 12/2008 | Shturman | |
| 2009/0018564 A1 | 1/2009 | Shturman | |
| 2009/0069829 A1 | 3/2009 | Shturman | |
| 2009/0182359 A1 | 7/2009 | Shturman | |
| 2009/0312777 A1 | 12/2009 | Shturman | |
| 2009/0318942 A1 | 12/2009 | Shturman | |
| 2009/0326568 A1 | 12/2009 | Shturman | |
| 2010/0010522 A1 | 1/2010 | Shturman | |
| 2010/0049226 A1 | 2/2010 | Shturman | |
| 2011/0054332 A1 | 3/2011 | Shturman | |
| 2012/0035633 A1 | 2/2012 | Shturman et al. | |
| 2012/0109170 A1 | 5/2012 | Shturman | |
| 2012/0191113 A1 | 7/2012 | Shturman | |
| 2013/0178881 A1 | 7/2013 | Shturman | |
| 2013/0245654 A1 | 9/2013 | Shturman | |
| 2013/0274773 A1 | 10/2013 | Shturman | |
| 2013/0296904 A1 | 11/2013 | Shturman | |
| 2013/0296905 A1 | 11/2013 | Shturman | |
| 2013/0310589 A1 | 11/2013 | Shturman | |

FOREIGN PATENT DOCUMENTS

| | | |
|---|---|---|
| EP | 1 820 458 | 8/2007 |
| WO | WO 98/50101 | 11/1998 |
| WO | WO 99/44513 | 9/1999 |
| WO | WO 01/15759 | 3/2001 |
| WO | WO 02/09599 | 2/2002 |
| WO | WO 2006/126076 | 11/2006 |
| WO | WO 2006/126175 | 11/2006 |
| WO | WO 2006/126176 | 11/2006 |

OTHER PUBLICATIONS

Declaration of Dmitri Prudnikov, Apr. 23, 2007, 1 page.
Excerpt from Deposition of Dmitri Prudnikov, Mar. 5, 2008, 7 pages.
Excerpt from Deposition of Dmitri Prudnikov, Mar. 6, 2008, 54 pages.
Exhibits Nos. 14, 31 & 32, from Deposition of Dmitri Prudnikov, Mar. 5, 2008, 3 pages.
Exhibits Nos. 33-39 from Deposition of Dmitri Prudnikov, Mar. 6, 2008, 47 pages.
International Search Report, corresponding to Int'l Application No. PCT/EP2007/062777 (dated Sep. 4, 2008).

* cited by examiner

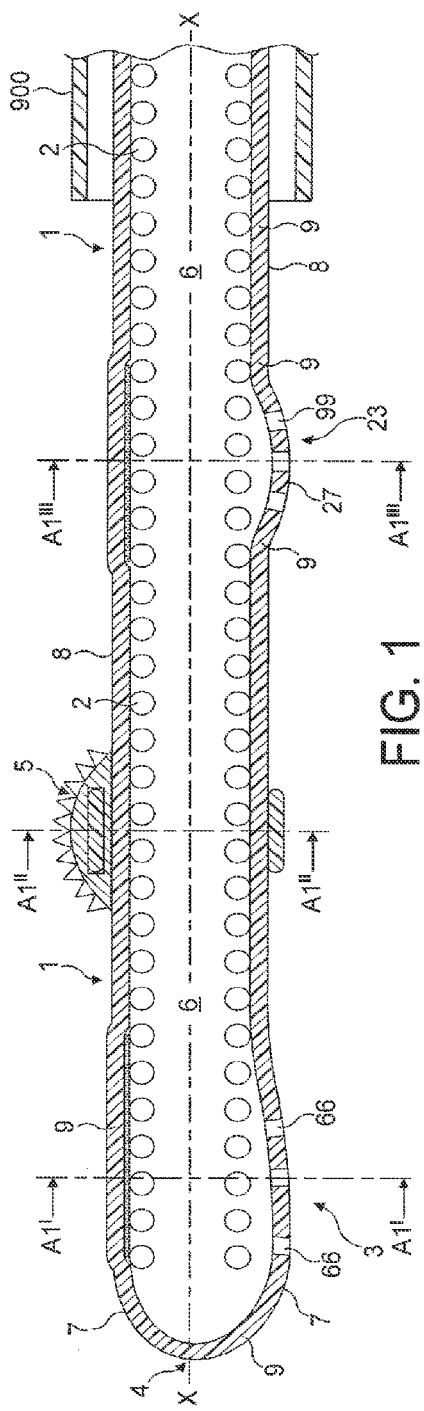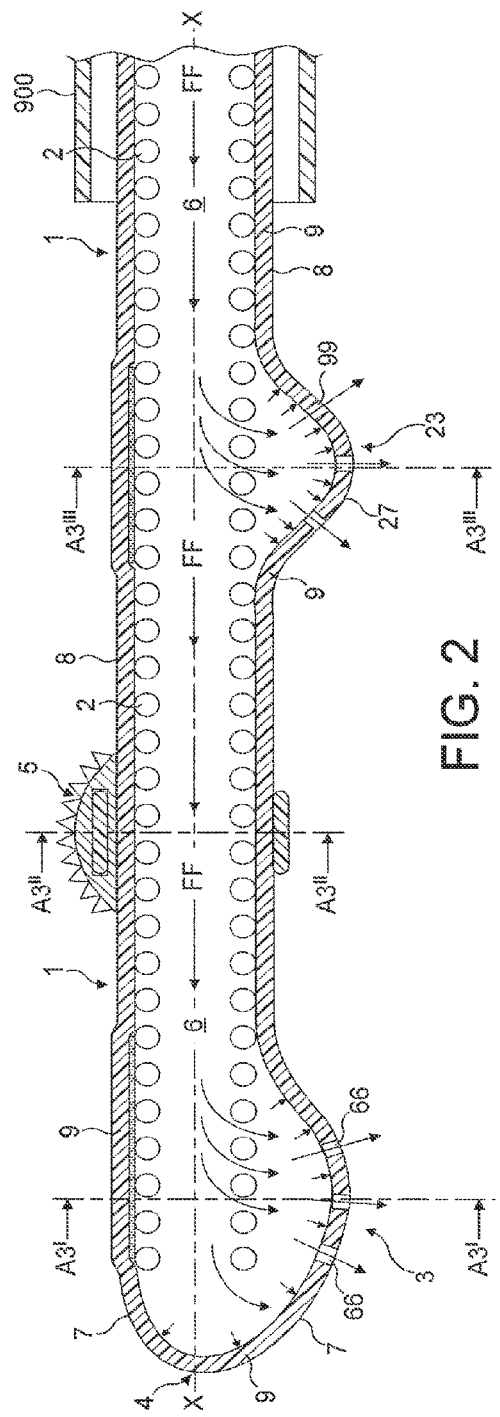

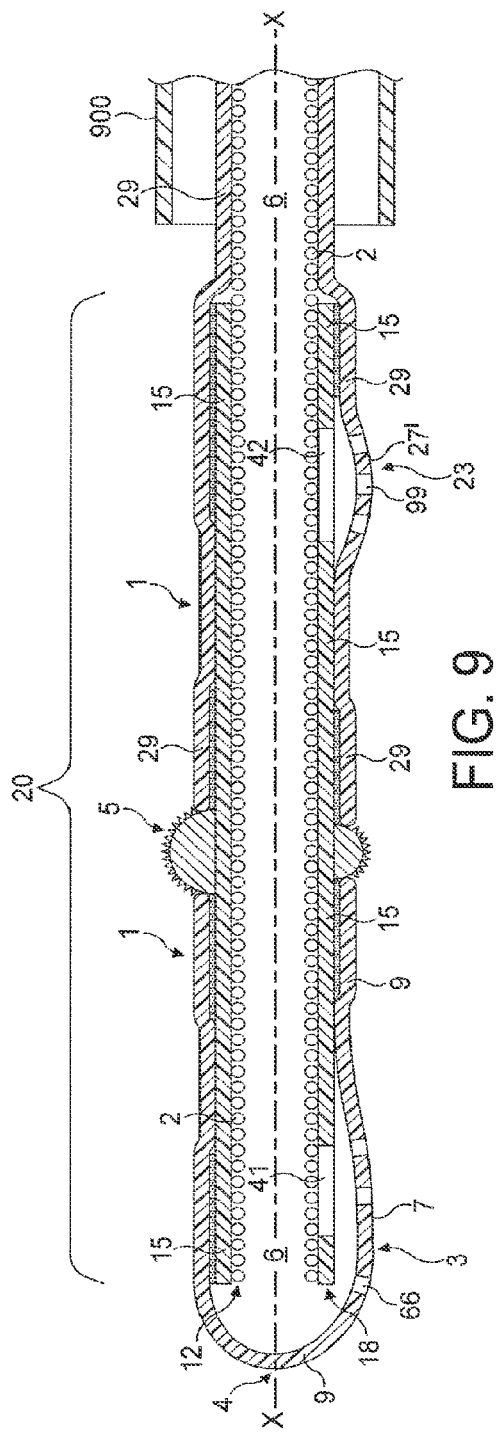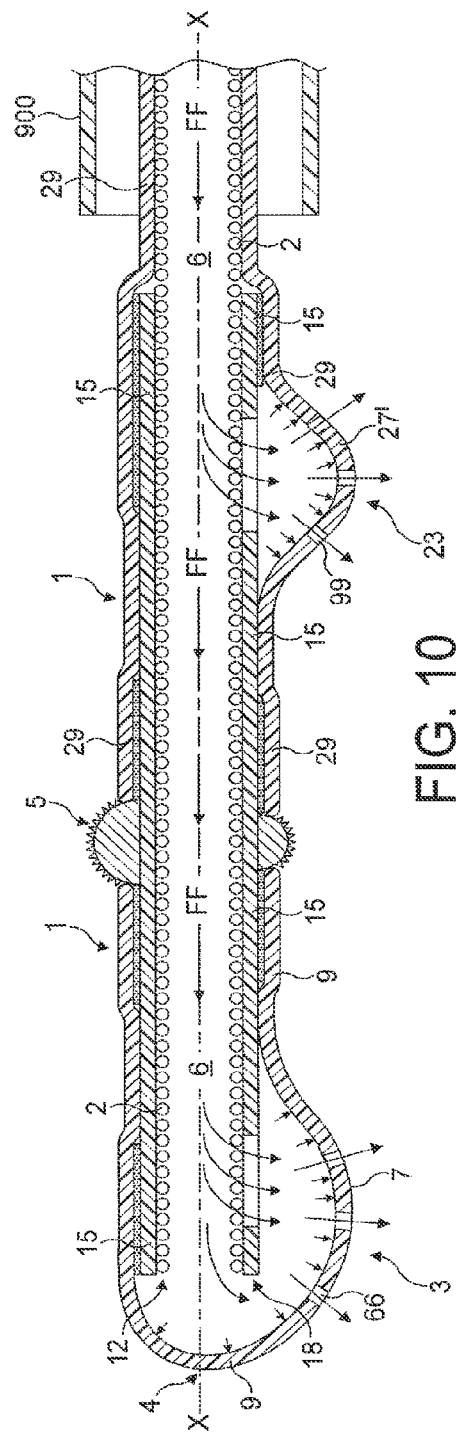

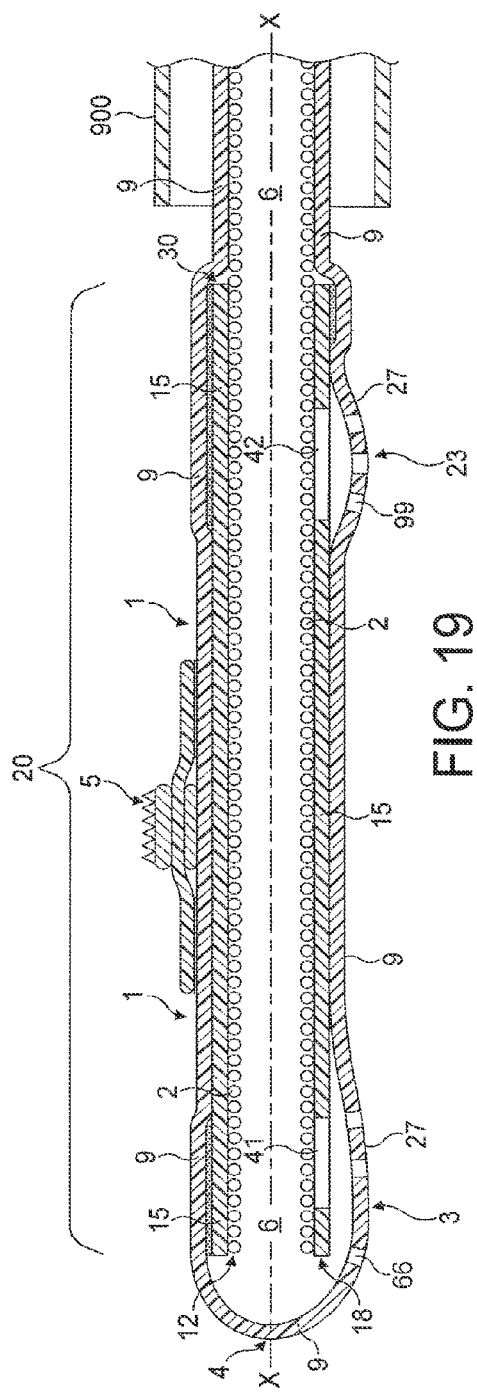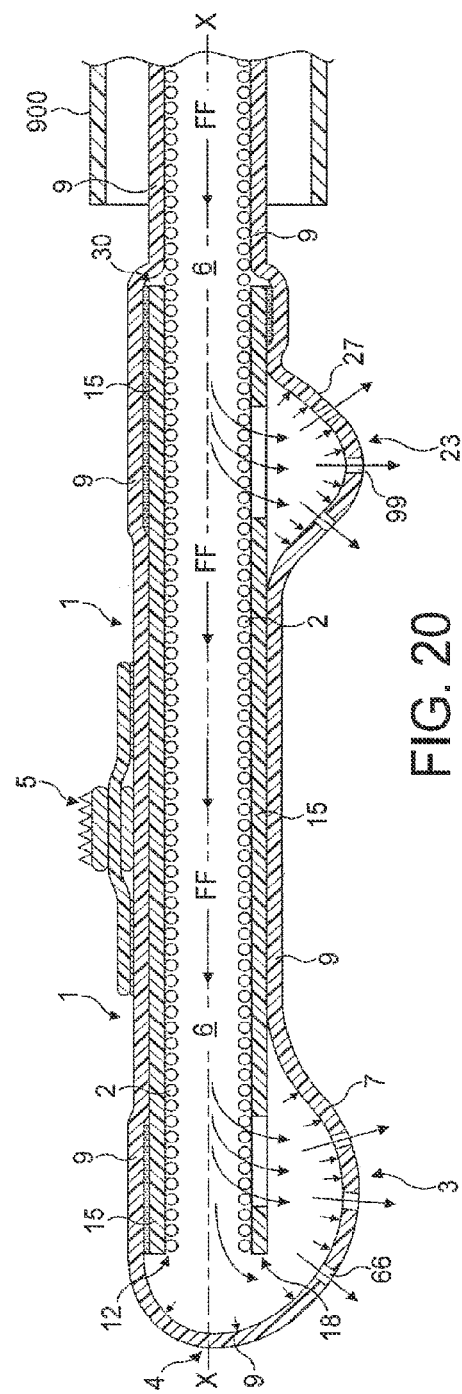

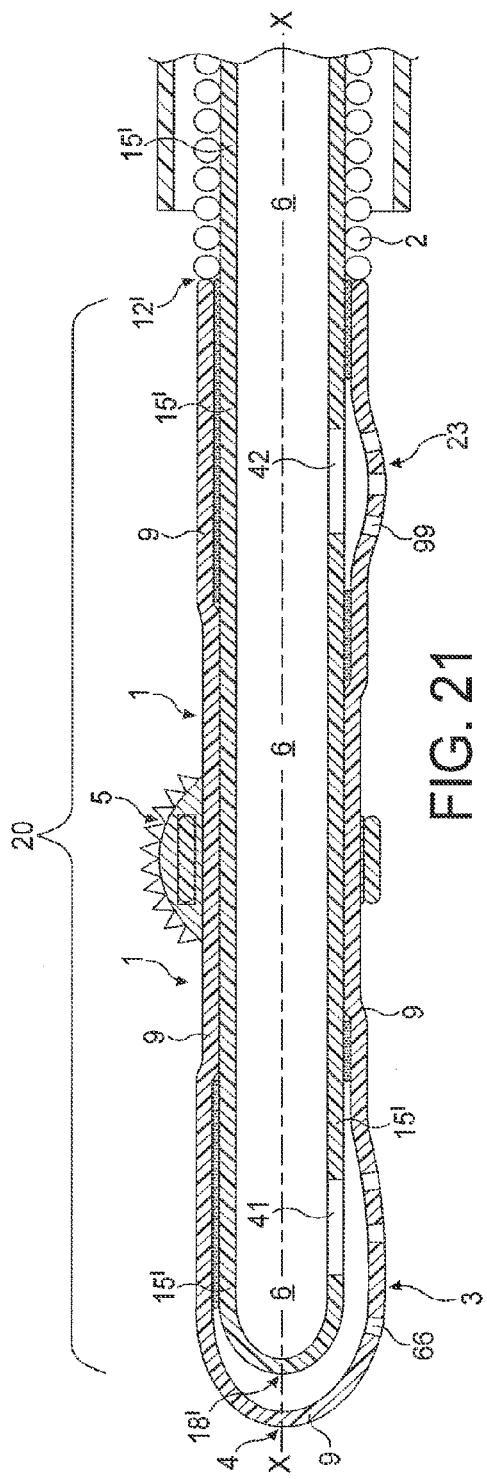
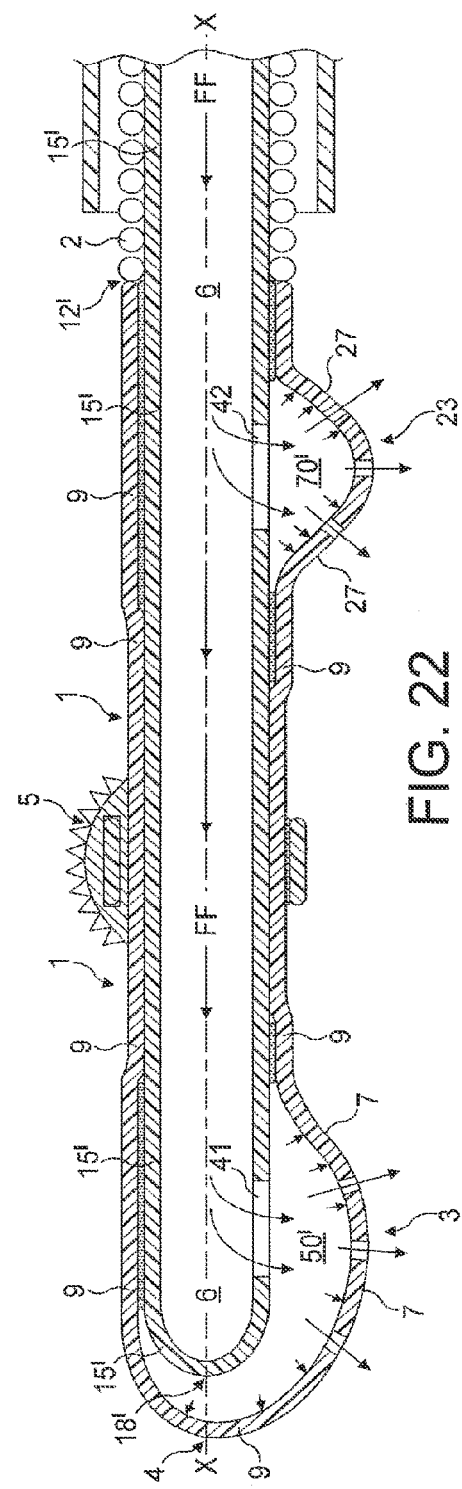

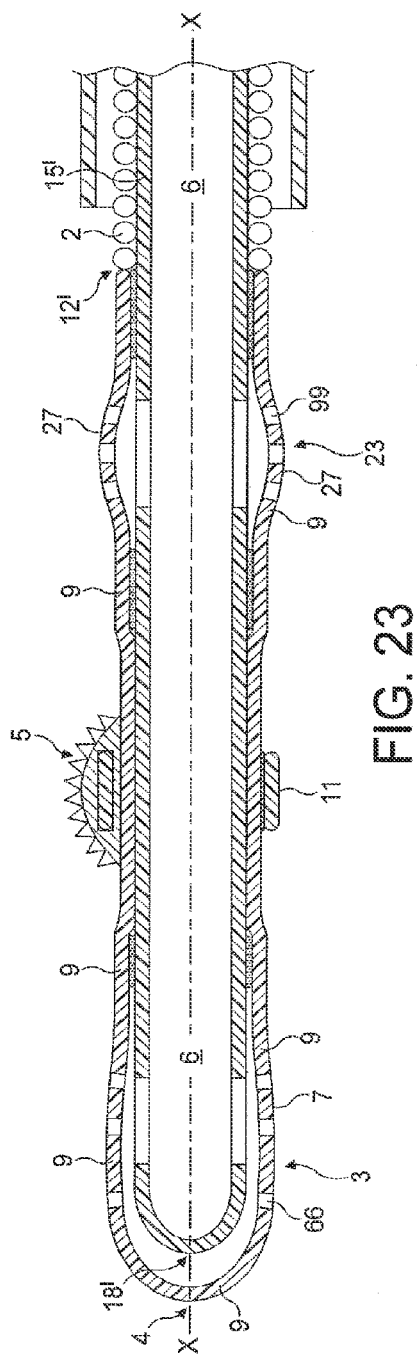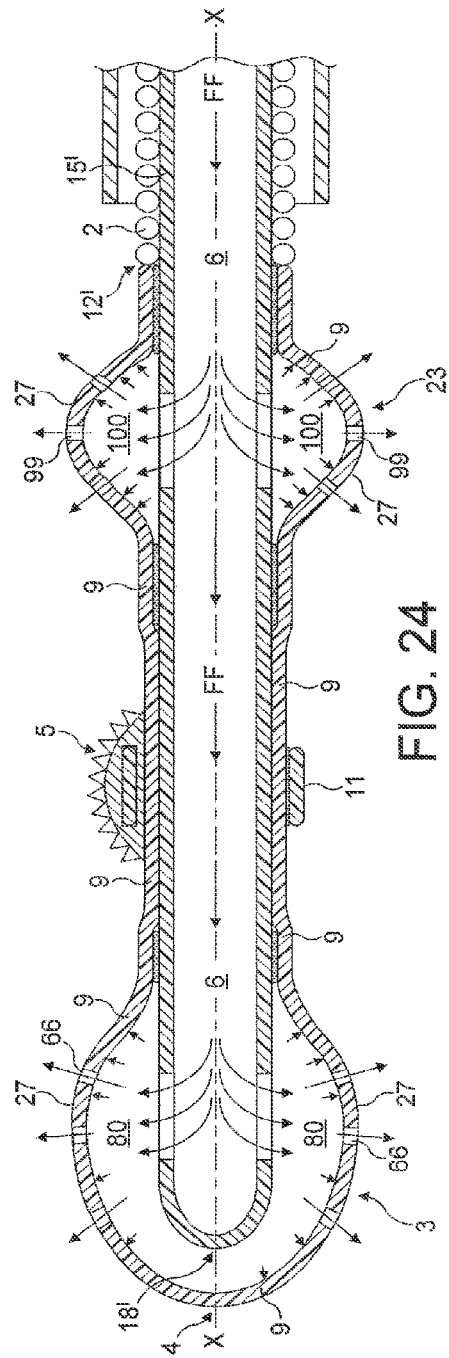

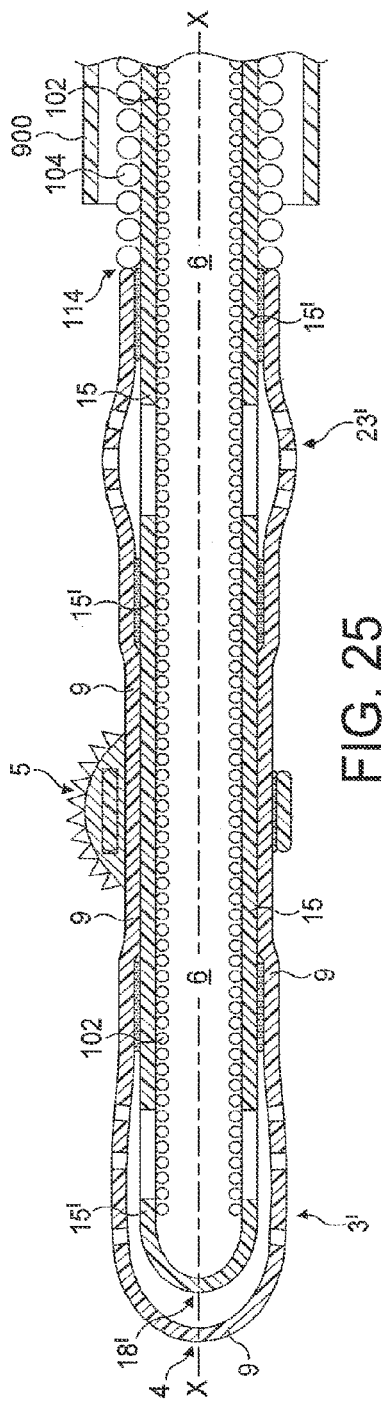
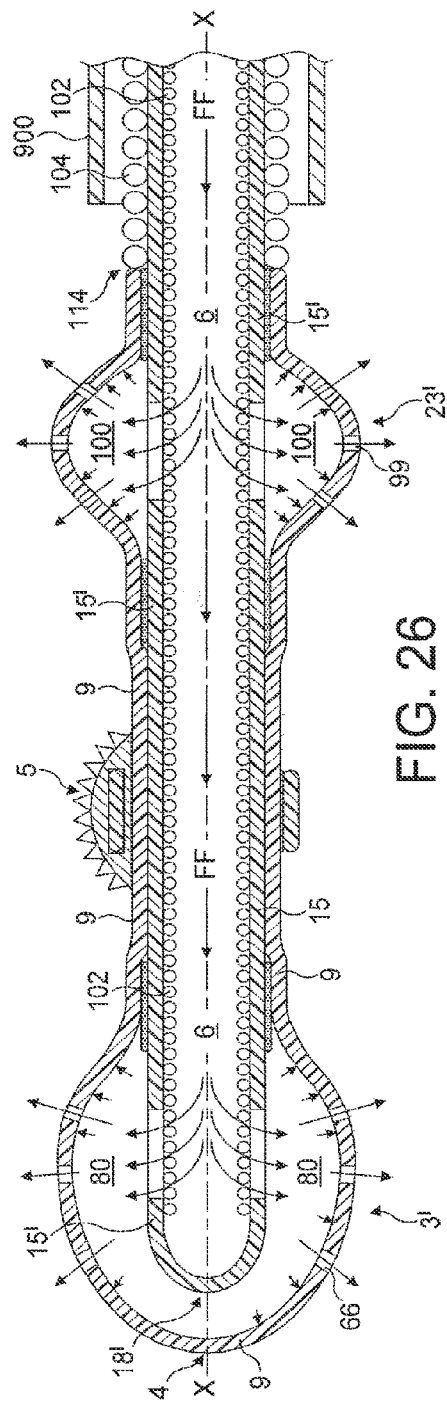
FIG. 25
FIG. 26

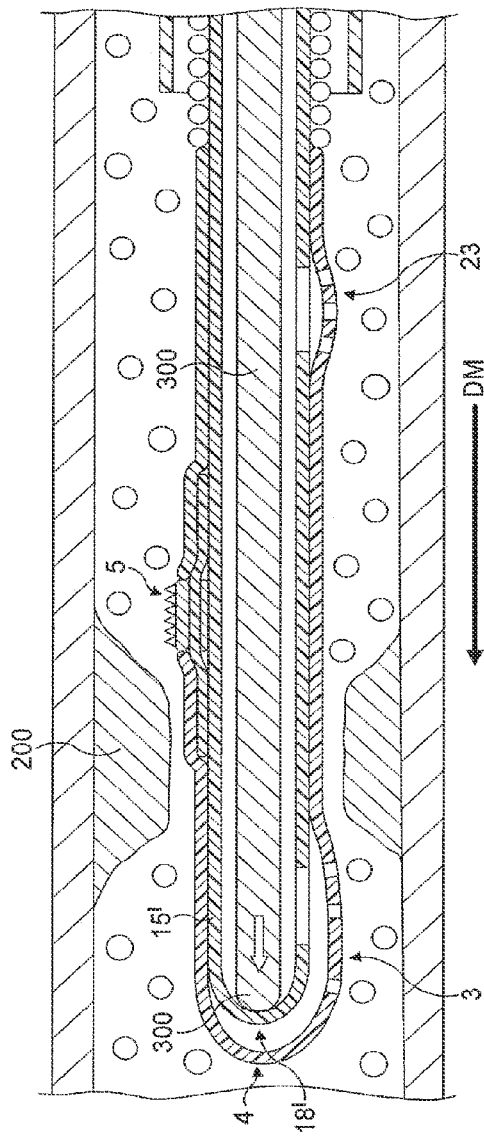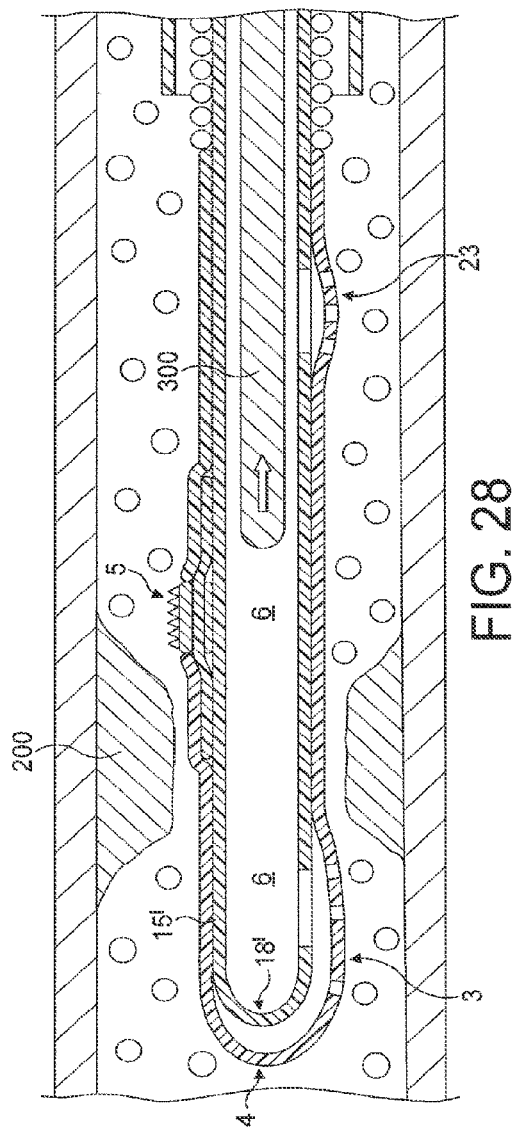

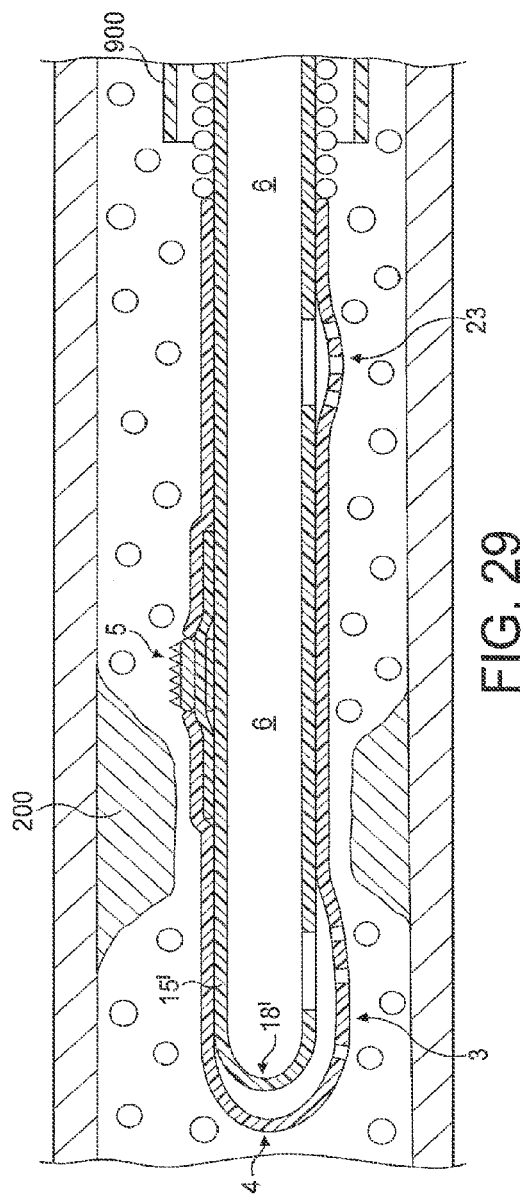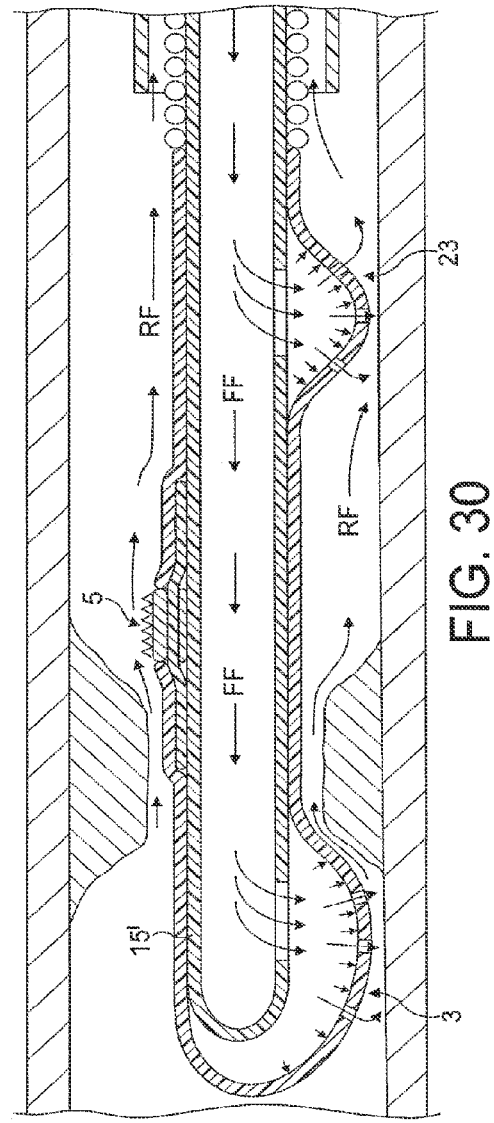

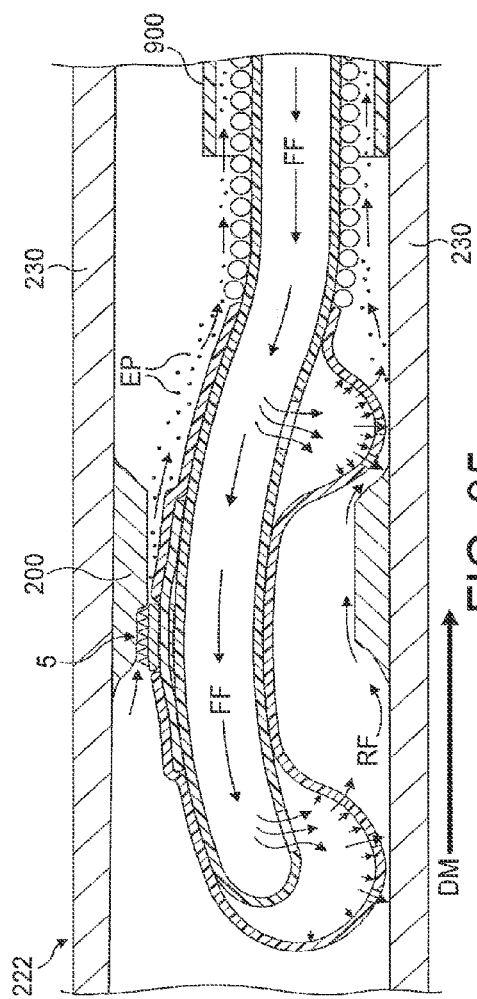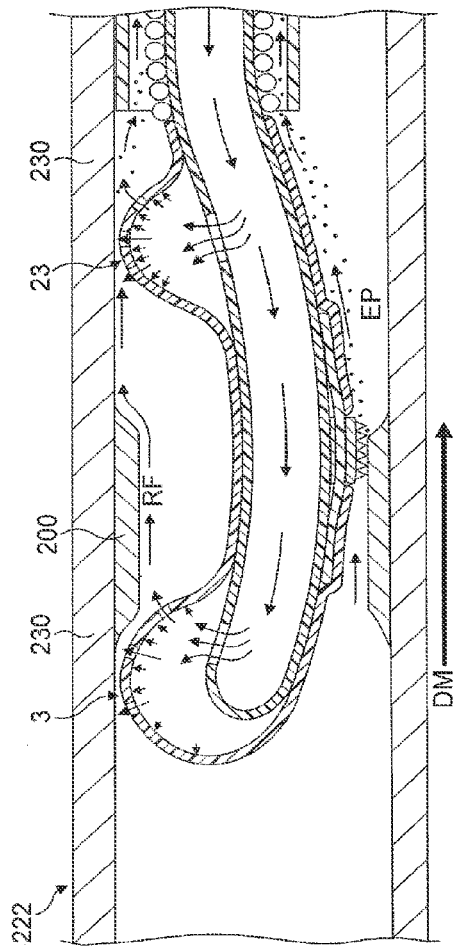

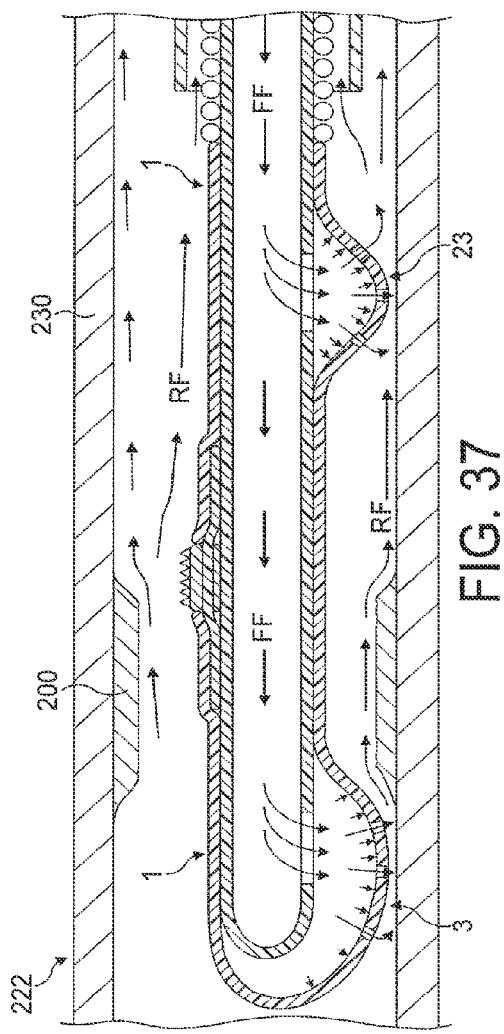
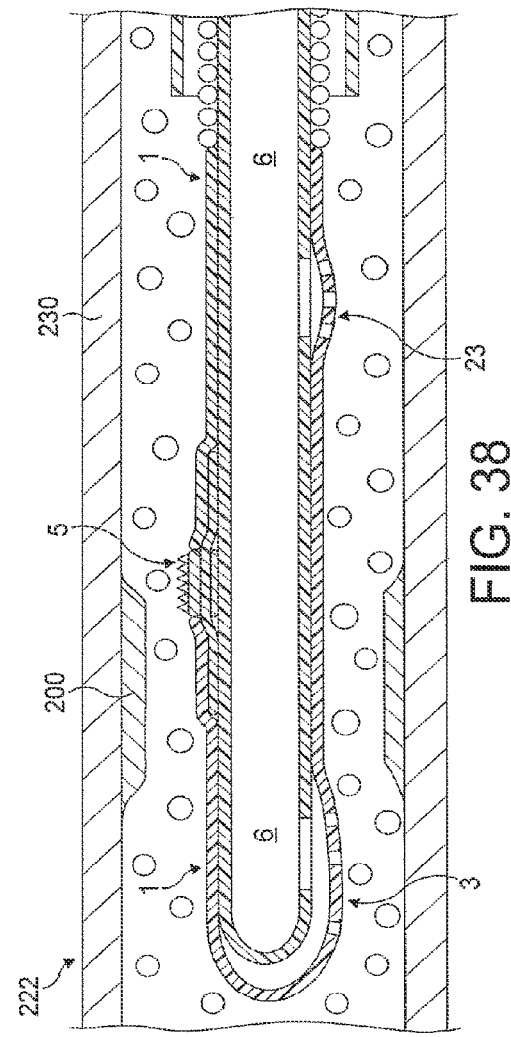
FIG. 37
FIG. 38

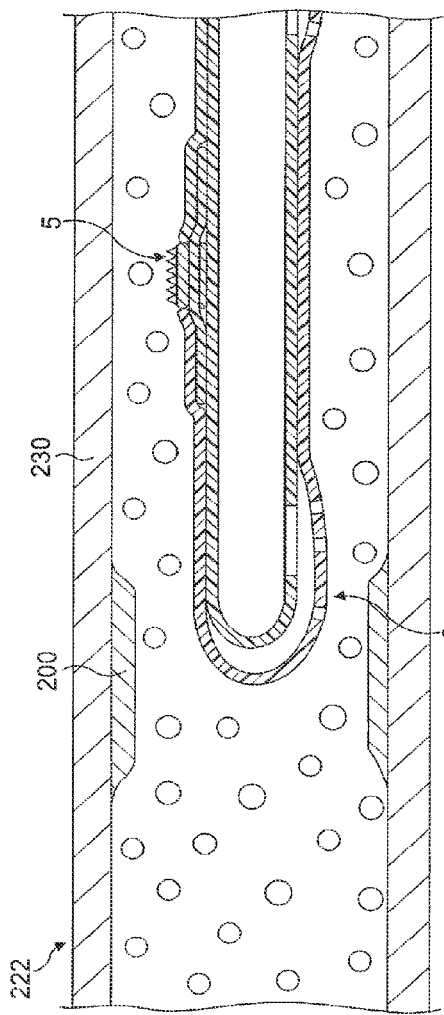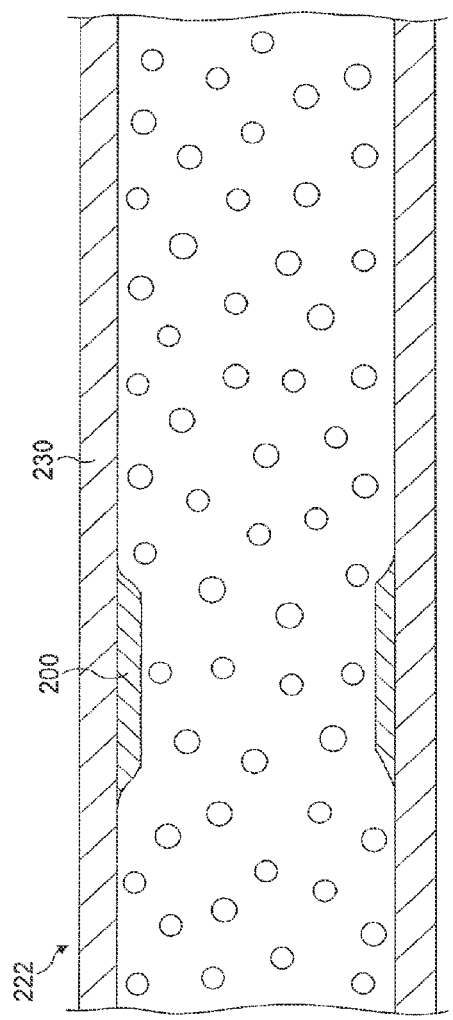

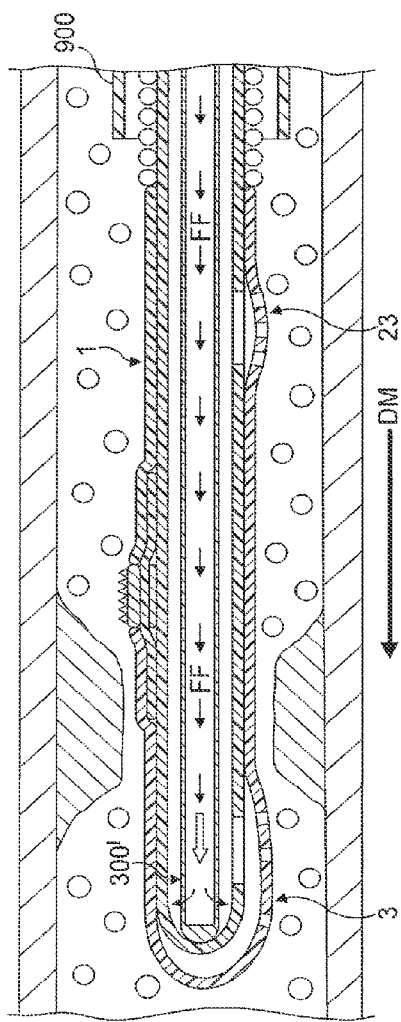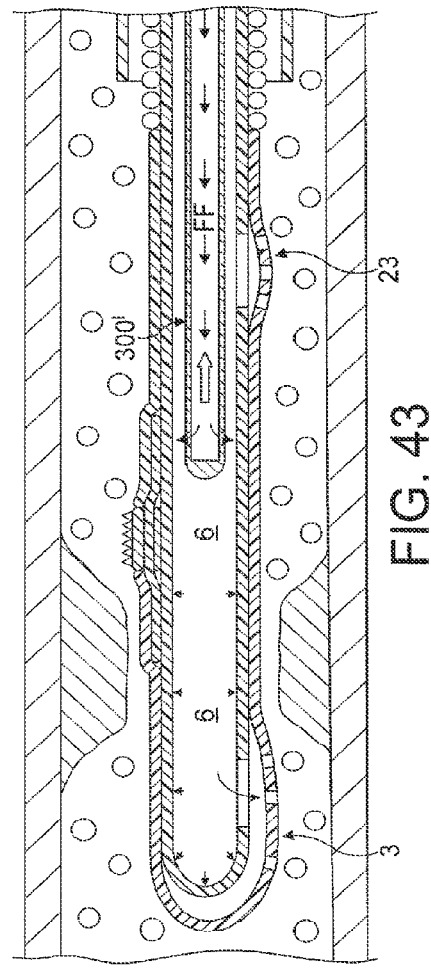

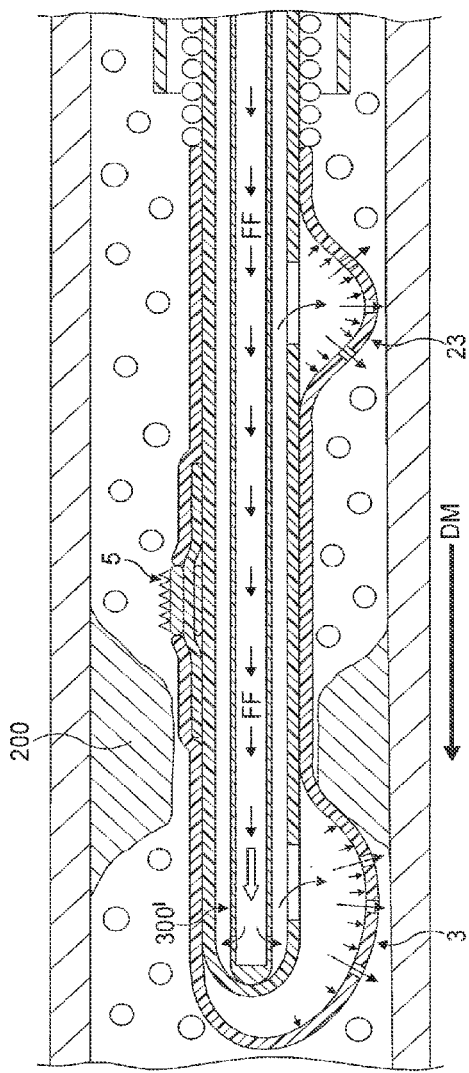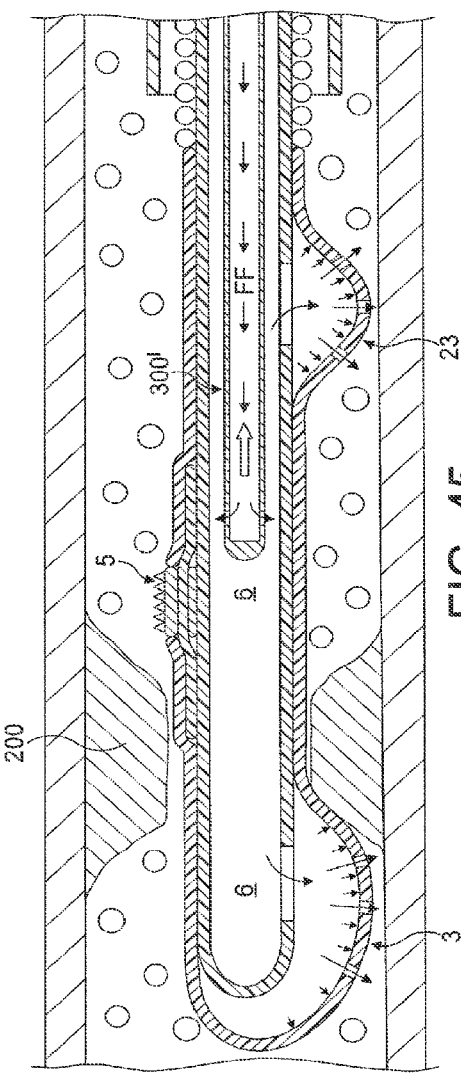

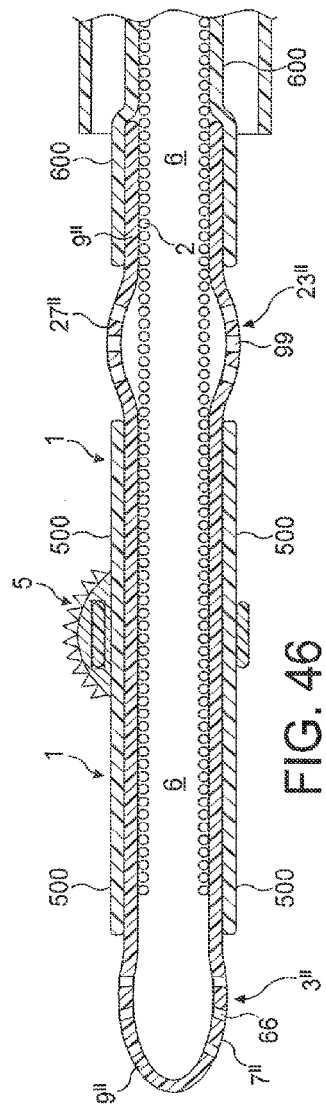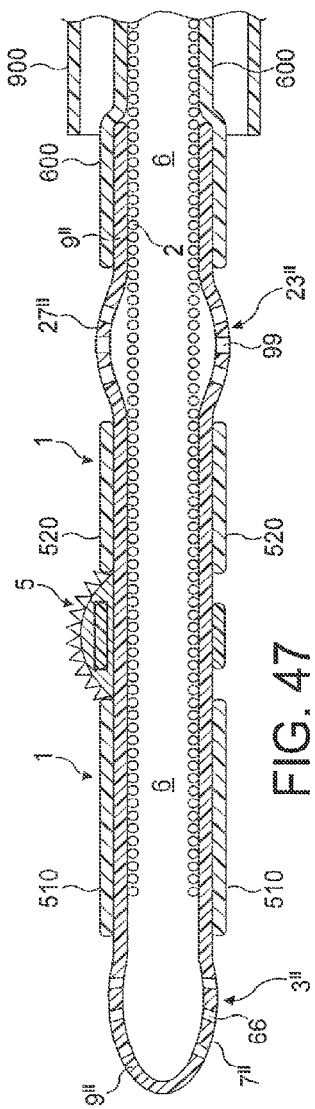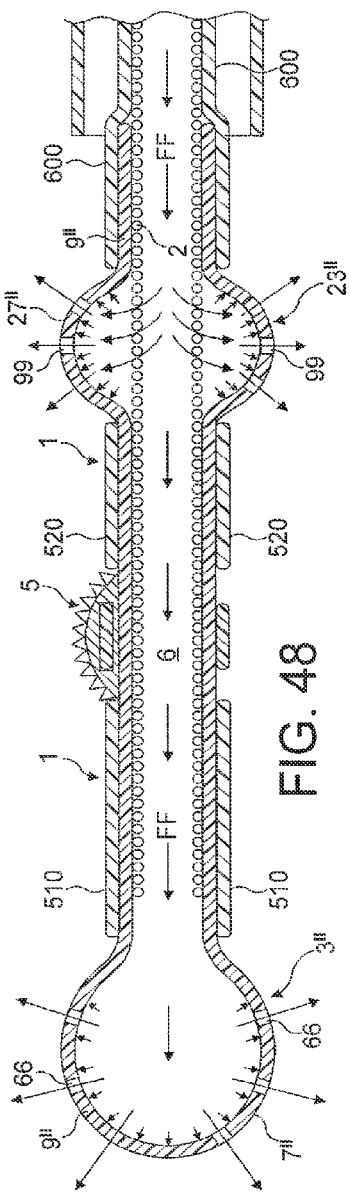

ROTATIONAL ATHERECTOMY DEVICE WITH FLUID INFLATABLE SUPPORT ELEMENTS AND DISTAL PROTECTION CAPABILITY

CROSS-REFERENCE TO RELATED APPLICATION

This application is a continuation of U.S. application Ser. No. 14/189,315 filed on Feb. 25, 2014, which is a continuation of U.S. application Ser. No. 13/783,993 filed on Mar. 4, 2013 (now U.S. Pat. No. 8,663,195), which is a continuation of U.S. application Ser. No. 13/344,993 filed on Jan. 6, 2012 (now U.S. Pat. No. 8,388,637), which is a continuation of U.S. application Ser. No. 12/515,524 filed on May 19, 2009 (now U.S. Pat. No. 8,109,955), which is a national phase application based on PCT/EP2007/062777 filed on Nov. 23, 2007 (published as PCT Pub. No. WO2008/062069), which claims priority of GB Patent Application No. 0623366.2 filed on Nov. 23, 2006, the contents of these prior applications being incorporated herein by reference.

TECHNICAL FIELD

The present invention relates to a rotational atherectomy device for removing or reducing stenotic lesions in blood vessels such as a human artery by rotating an abrasive element within the vessel to partially or completely ablate the unwanted material.

BACKGROUND

Atherosclerosis, the clogging of arteries, is a leading cause of coronary heart disease. Blood flow through the peripheral arteries (e.g., carotid, femoral, renal etc.), is similarly affected by the development of atherosclerotic blockages. One conventional method of removing or reducing blockages in blood vessels is known as rotational atherectomy. A long guidewire is advanced into the diseased blood vessel and across the stenotic lesion. A hollow drive shaft formed from a torque transmitting coiled wire(s) is advanced over the guidewire. The distal end of the drive shaft terminates in a burr provided with an abrasive surface formed from diamond grit or diamond particles. The burr is positioned against the occlusion and the drive shaft rotated at extremely high speeds (e.g., 20,000-160,000 rpm).

As the burr rotates, the physician slowly advances it so that the abrasive surface of the burr scrapes against the occluding tissue and disintegrates it, reducing the occlusion and improving the blood flow through the vessel. Such a method and a device for performing the method are described in, for example, U.S. Pat. No. 4,990,134 to Auth. It is also known from U.S. Pat. No. 6,132,444 to Shturman (the instant inventor) et al., to provide a drive shaft which is also formed from a single layer of torque transmitting coiled wire or wires but different to the device described in U.S. Pat. No. 4,990,134 to Auth, mentioned above, by providing the drive shaft with an eccentric enlarged diameter section located proximally to and spaced away from the distal end of the drive shaft. This drive shaft is formed from a single layer of torque transmitting coiled wire(s). According to U.S. Pat. No. 6,132,444 to Shturman, abrasive particles are located around a maximum diameter of the eccentric segment of the drive shaft thereby forming an eccentric abrasive element positioned proximally to and spaced away from the distal end of the drive shaft.

A rotational atherectomy device with distal embolic protection capability is known from WO 2006/126076 to Shturman (the current inventor). In one preferred embodiment of this known Shturman application the distal end of the fluid impermeable drive shaft is advanced across the stenotic lesion to be treated and flushing fluid is pumped through the drive shaft in an antegrade direction to enter the vessel through at least one luminal opening located distally to the abrasive element. As a result of a continued flow of flushing fluid into the vessel in this way, a fluid pressure is generated in the vessel distal to the abrasive element which is sufficient to generate a retrograde flow of at least a portion of the flushing fluid around the abrasive element and the fluid impermeable drive shaft. This retrograde flowing flushing fluid entrains stenotic debris abraded by the rotating abrasive element and flows into a lumen of stationary drive shaft sheath thereby preventing distal migration of debris along the treated vessel. In the most preferred embodiment, abraded debris are not only being removed from the treated vessel but from the patient altogether.

According to the preferred embodiments of WO 2006/126076, it is also possible to provide inflatable support elements located distal and proximal to the abrasive element. The inflatable support elements may have centers of mass which are offset from the longitudinal axis of the drive shaft. Such support elements act as counterweights to the eccentric abrasive element, i.e. an abrasive element that has its centre of mass offset from the longitudinal axis of the drive shaft. Alternatively, the abrasive element and the support elements may have centers of mass which lie along the longitudinal axis of the drive shaft.

The rotational atherectomy device with fluid inflatable support elements has a smaller crossing profile than the rotational atherectomy device with solid support elements. The term 'crossing profile' refers to a maximum cross-sectional dimension of that portion of the device which has to be advanced across the stenotic lesion. All embodiments of the device described in WO 2006/126076 have to be advanced along the treated vessel and across the stenotic lesion over the guidewire. The devices with fluid inflatable support elements known from WO 2006/126076 allow to reduce the crossing profile of the drive shaft of the device but they still have to be advanced across the stenotic lesion over the guidewire. The outer diameter of the drive shaft of any rotational atherectomy device with distal protection which is advanced over a guidewire may still be too large to cross very tight stenotic lesions. The present invention therefore seeks to provide a rotational atherectomy device with distal protection capability which does not require use of a guidewire for its advancement across the stenotic lesion to be treated. Such device may have a crossing diameter which is smaller than the crossing diameter of known rotational atherectomy devices with distal protection capability. The present invention also seeks to provide a rotational atherectomy device with distal protection capability that does not require occlusion of a distal end of the guidewire lumen prior to initiating flow of pressurized fluid through the guidewire lumen.

SUMMARY

According to the present invention, there is provided a rotational atherectomy device for abrading a stenotic lesion from a vessel of a patient comprising a flexible drive shaft which extends towards a distal end of the device, a distal fluid inflatable support element located at a distal end of the drive shaft and an abrasive element mounted to the drive shaft proximal to and spaced away from the distal fluid inflatable support element, both the abrasive element and the distal fluid inflatable support element being rotatable together with the drive shaft, the drive shaft comprising a torque transmitting coil which defines a long lumen of the drive shaft, the distal fluid inflatable support element being formed from a fluid impermeable membrane that crosses a longitudinal axis common to the torque transmitting coil and the lumen of the drive shaft at the distal end of the device, thereby preventing pressurized fluid flowing along the lumen of the drive shaft from entering the vessel in the direction of said longitudinal axis so that fluid has to pass through the fluid inflatable support element, inflating said support element and exiting from the device through an outflow opening in the fluid inflatable support element in a direction different from the direction of the longitudinal axis of the coil and the lumen.

Preferably, this fluid impermeable membrane forms a wall of the distal fluid inflatable support element.

Preferably, the wall of the distal fluid inflatable support element extends around the torque transmitting coil of the drive shaft.

The wall of the distal fluid inflatable support element is preferably bonded to a surface of the torque transmitting coil proximal to the distal fluid inflatable support element.

In a preferred embodiment, the torque transmitting coil comprises at least one space which separates individual windings of the coil, said space allowing fluid communication between the lumen of the drive shaft and the distal fluid inflatable support element.

A preferred embodiment comprises an anchoring sleeve underlying the fluid impermeable membrane along at least a distal end portion of the drive shaft, the fluid impermeable membrane being attached to said anchoring sleeve proximal to the distal fluid inflatable support element.

Preferably, the torque transmitting coil has proximal and distal ends and an anchoring sleeve is disposed around at least a distal end portion of the torque transmitting coil.

Preferably, the torque transmitting coil has proximal and distal ends and the anchoring sleeve extends distally from the distal end of the coil such that the distal inflatable support element formed around the anchoring sleeve from the fluid impermeable membrane is spaced away from the distal end of the torque transmitting coil, the abrasive element being disposed around at least a portion of the circumference of the anchoring sleeve.

In an embodiment with one torque transmitting coil, the anchoring sleeve may extend proximally within and line the torque transmitting coil.

Preferably, the drive shaft comprises inner and outer torque transmitting coils, the anchoring sleeve being sandwiched between said inner and outer torque transmitting coils, the anchoring sleeve and the inner torque transmitting coil extending distally from a distal end of the outer torque transmitting coil, the abrasive element being disposed around at least a portion of the circumference of the anchoring sleeve.

Preferably, the anchoring sleeve is closed at its distal end.

Preferably, the anchoring sleeve has an opening therein associated with the distal fluid inflatable support element to allow pressurised fluid to flow through said opening into the distal fluid inflatable support element from the lumen of the drive shaft.

Preferably, the distal end of the device and the closed distal end of the sleeve are spaced away from each other to form a soft atraumatic cushion between the distal end of the device and the closed distal end of the anchoring sleeve.

Preferably, the device comprises an elongate core element advanceable through the lumen of the drive shaft to stiffen the drive shaft and which assists in the advancement of the drive shaft along the vessel towards the treatment site.

The elongate core element preferably has a distal end configured for operational engagement with the distal end of the anchoring sleeve.

Preferably, the elongate core element is configured to be removed from the device after the distal end of the device has been advanced to the treatment site so that a detachable fluid supply tube can be attached to the device.

The elongate core element preferably includes a lumen for the passage of fluid therealong.

Preferably, the elongate core element has at least one opening located at or proximal to its distal end, said opening providing fluid communication between the lumen of the elongate core element and the lumen of the drive shaft.

The anchoring sleeve is preferably formed from a fluid impermeable membrane.

Preferably, the anchoring sleeve comprises at least one opening located proximal to the closed distal end of the sleeve, said opening providing fluid communication between the lumen of the drive shaft and the distal fluid inflatable support element.

Preferably, the distal fluid inflatable support element has, when inflated, a centre of mass which lies along the longitudinal axis of the torque transmitting coil and the lumen of the drive shaft.

Preferably, a fluid inflatable space within the distal fluid inflatable support element extends uniformly around the longitudinal axis of the torque transmitting coil and the lumen of the drive shaft to provide the distal support element with a centre of mass which lies along the longitudinal axis of the torque transmitting coil and the lumen of the drive shaft when said distal support element is fluid inflated.

Preferably, there is a plurality of openings in the wall of the fluid inflatable distal support element, said openings being located around the circumference of the wall of the fluid inflatable distal support element such that, during rotation of the drive shaft, at least some of said openings face an inner surface of a treated vessel, so that flows of fluid through the openings form a layer of fluid between the outer wall of the fluid inflated distal support element and a wall of the treated vessel, said layer of fluid forming a fluid bearing between the outer wall of the rotating fluid inflated distal support element and the wall of the treated vessel.

Preferably, the rotational atherectomy device comprises a proximal fluid inflatable support element located proximal to and spaced away from the abrasive element, the proximal fluid inflatable support element having an outer wall.

Preferably, the outer wall of the proximal fluid inflatable support element is continuous and integral with the fluid impermeable membrane.

Preferably, the proximal fluid inflatable support element has, when inflated, a centre of mass which lies along the longitudinal axis of the torque transmitting coil and the lumen of the drive shaft.

Preferably, a fluid inflatable space within the proximal fluid inflatable support element extends uniformly around a longitudinal axis of the torque transmitting coil and the lumen of the drive shaft to provide the proximal support element with a centre of mass which lies along the longitudinal axis of the torque transmitting coil and the lumen of the drive shaft when said proximal support element is fluid inflated.

Preferably, there is a plurality of openings in the wall of the fluid inflatable proximal support element, said openings being located around the circumference of the wall of the fluid inflatable proximal support element such that, during rotation of the drive shaft, at least some of said openings face an inner surface of a treated vessel, so that flows of fluid through the openings form a layer of fluid between the outer wall of the fluid inflated proximal support element and a wall of the treated vessel, said layer of fluid forming a fluid bearing between the outer wall of the rotating fluid inflated proximal support element and the wall of the treated vessel.

Preferably, the abrasive element has a centre of mass which lies on the longitudinal axis of the torque transmitting coil and the lumen of the drive shaft.

In a modified embodiment, the abrasive element may have a centre of mass which is offset in a radial direction from the longitudinal axis of the torque transmitting coil and the lumen of the drive shaft.

In an alternative embodiment of the invention, the centre of mass of the abrasive element is always offset in a radial direction from the longitudinal axis of the torque transmitting coil and the lumen of the drive shaft.

In the alternative embodiment, the distal fluid inflatable support element has, when inflated, a centre of mass which is offset in a radial direction from the longitudinal axis of the torque transmitting coil and the lumen of the drive shaft.

Preferably in the alternative embodiment, the centre of mass of the distal fluid inflatable support element and the centre of mass of the abrasive element are offset from the longitudinal axis of the torque transmitting coil and the lumen of the drive shaft in opposite directions.

In the alternative embodiment, preferably, the wall of the distal fluid inflatable support element is bonded to a segment of a circumference of the torque transmitting coil, a middle point of said segment being spaced from the longitudinal axis of the coil and the lumen of the drive shaft in the same direction as the centre of mass of the abrasive element.

In the alternative embodiment, preferably, the wall of the distal fluid inflatable support element defines a fluid inflatable space that extends only partially around a circumference of the torque transmitting coil so that, when the distal inflatable support element is fluid inflated, its centre of mass is offset from a longitudinal axis of the torque transmitting coil and the lumen of the drive shaft in one direction, the distal fluid inflated support element acting, during rotation of the drive shaft, as a counterweight to the abrasive element which has its centre of mass offset from the longitudinal axis of the torque transmitting coil and the lumen of the drive shaft in the opposite direction.

In the alternative embodiment, the abrasive element preferably has a centre of mass which is offset in a radial direction from the longitudinal axis of the torque transmitting coil and the lumen of the drive shaft, the wall of the distal fluid inflatable support element defining a fluid inflatable space that extends only partially around a circumference of the anchoring sleeve so that, when the distal inflatable support element is fluid inflated, its centre of mass is offset from the longitudinal axis of the torque transmitting coil and the lumen of the drive shaft in a direction opposite to the direction in which the centre of mass of the abrasive element is offset from the longitudinal axis of the torque transmitting coil and the lumen of the drive shaft, the distal fluid inflated support element acting, during rotation of the drive shaft, as a counterweight to the abrasive element.

Preferably, the alternative embodiment comprises a proximal fluid inflatable support element located proximal to and spaced away from the abrasive element, the proximal fluid inflatable support element having an outer wall which is bonded to a segment of the circumference of the torque transmitting coil, a middle point of said segment being spaced from the from the longitudinal axis of the torque transmitting coil and the lumen of the drive shaft in the same direction as the centre of mass of the abrasive element.

Preferably, the rotational atherectomy device of the alterative embodiment comprises a proximal fluid inflatable support element located proximal to and spaced away from the abrasive element, the proximal fluid inflatable support element having an outer wall which defines a fluid inflatable space that extends only partially around a circumference of the anchoring sleeve so that, when the proximal inflatable support element is fluid inflated, its centre of mass is offset from a longitudinal axis of the torque transmitting coil and the lumen of the drive shaft in a direction opposite to the direction in which the centre of mass of the abrasive element is offset from the longitudinal axis of the torque transmitting coil and the lumen of the drive shaft, the proximal fluid inflated support element acting, during rotation of the drive shaft, as a counterweight to the abrasive element.

Preferably, in the alternative embodiment, the abrasive element has a centre of mass which is offset in a radial direction from the longitudinal axis of the torque transmitting coil and lumen of the drive shaft, the walls of the distal and proximal fluid inflatable support elements defining fluid inflatable spaces that extend only partially around a circumference of the torque transmitting coil so that, when the inflatable support elements are fluid inflated, their centers of mass are offset from the longitudinal axis of the torque transmitting coil and the lumen of the drive shaft a direction opposite to the direction in which the centre of mass of the abrasive element is offset from the longitudinal axis of the torque transmitting coil and the lumen of the drive shaft, the fluid inflated support elements acting, during rotation of the drive shaft, as a counterweights to the abrasive element.

Preferably, in the alternative embodiment, the wall of the distal fluid inflatable support element has an outflow opening located such that said outflow opening, during rotation of the drive shaft, faces an inner surface of a treated vessel so that fluid flowing through the outflow opening forms a layer of fluid between the outer wall of the rotating fluid inflated distal support element and a wall of the treated vessel, said layer of fluid forming a fluid bearing between the outer wall of the rotating fluid inflated distal support element and the wall of the treated vessel.

Preferably, in the alternative embodiment, at least a few openings in the outer wall of a rotating fluid inflated distal support element are located around a circumference of the wall of the inflated distal support element such that at any time during rotation of the drive shaft at least one of said few openings is facing an inner surface of a treated vessel, so that a flow of fluid through the opening forms a layer of fluid between the wall of the rotating fluid inflated distal support element and a wall of the treated vessel, said layer of fluid forming a fluid bearing between the wall of the rotating fluid inflated support element and the wall of the treated vessel.

Preferably, in the alternative embodiment, at least one opening in the wall of a rotating fluid inflated proximal support element is located such that at any time during rotation of the drive shaft said opening is facing an inner surface of a treated vessel, so that a flow of fluid through the opening forms a layer of fluid between the wall of the rotating fluid inflated proximal support element and a wall of the treated vessel, said layer of fluid forming a fluid bearing between the wall of the rotating fluid inflated proximal support element and the wall of the treated vessel.

Preferably, in the alternative embodiment, at least a few openings in the outer wall of a rotating fluid inflated proximal support element are located around circumference of the wall of the inflated distal support element such that at any time during rotation of the drive shaft at least one of said few openings is facing an inner surface of a treated vessel, so that a flow of fluid through the opening forms a layer of fluid between the wall of the rotating fluid inflated proximal support element and a wall of the treated vessel, said layer of fluid forming a fluid bearing between the wall of the rotating fluid inflated support element and the wall of the treated vessel.

Preferably, the walls of both inflatable support elements are made from a continuous stretchable membrane, said fluid impermeable stretchable membrane being sandwiched between the torque transmitting coil and at least one nonstretchable sleeve, the non-stretchable sleeve being disposed around the stretchable membrane between the fluid inflatable support elements. Preferably, the non-stretchable sleeve is formed in two sections, each section being disposed on either side of the abrasive element. Preferably, a second long, non-stretchable sleeve overlaps the stretchable membrane for a short distance proximal to the proximal fluid inflatable support element and extends in a proximal direction around the torque transmitting coil towards the proximal end of the drive shaft. Preferably, the non-stretchable sleeve is fluid impermeable.

Preferably, in the above-described alternative embodiment, the abrasive element has a centre of mass which is spaced away from the longitudinal axis of the torque transmitting coil and the lumen of the drive shaft, and an anchoring sleeve is disposed around the torque transmitting coil at least along a length of the drive shaft occupied by fluid inflatable support elements, said anchoring sleeve being disposed over the coil under the fluid impermeable membrane which forms fluid inflatable support elements, the fluid impermeable membrane along a length of the fluid inflatable support elements being bonded to the anchoring sleeve only along one side of a circumference of the drive shaft, thereby preventing the fluid inflatable support elements from expanding uniformly around an entire circumference of the anchoring sleeve when fluid inflated so as to form fluid inflated counterweights with centers of mass spaced radially away from a longitudinal axis of the torque transmitting coil and the lumen of the drive shaft in a direction opposite to the direction in which the centre of mass of the abrasive element is spaced away from the longitudinal axis of the torque transmitting coil and the lumen of the drive shaft.

Preferably, the lumen of the drive shaft has proximal and distal portions, the proximal portion of the the lumen having a larger cross-sectional area relative to the cross-sectional area of the distal portion of the lumen so that per unit of length hydraulic resistance to fluid flow of the proximal portion of the lumen is less than the hydraulic resistance to fluid flow of the distal portion of the lumen.

Preferably, all the pressurised fluid which flows through the lumen of the drive shaft exits from the device into the vessel through opening(s) in the wall(s) of the fluid inflatable support elements.

Preferably, the abrasive element is spaced away from the distal end of the torque transmitting coil.

Preferably, in the rotational atherectomy device which has inner and outer torque transmitting coils, the abrasive element is spaced away from the distal end of the outer torque transmitting coil.

According to the present invention, there is provided a rotational atherectomy device for abrading a stenotic lesion from a vessel of a patient comprising a rotatable, flexible drive shaft, a distal fluid inflatable support element located at a distal end of the device and an abrasive element mounted to the drive shaft proximal to and spaced away from the distal fluid inflatable support element, both the abrasive element and the distal fluid inflatable support element being rotatable together with the drive shaft, the drive shaft comprising a torque transmitting coil which defines a long lumen of the drive shaft, the distal fluid inflatable support element being formed from a fluid impermeable membrane that crosses a longitudinal axis common to the torque transmitting coil and the lumen of the drive shaft at the distal end of the device, thereby preventing pressurized fluid flowing along the lumen of the drive shaft from entering the vessel in the direction of said longitudinal axis so that fluid has to pass through the fluid inflatable support element, inflating said support element and exiting from the device through an outflow opening in the fluid inflatable support element in a direction different from the direction of the longitudinal axis of the coil and the lumen.

In one preferred embodiment, the abrasive element has a centre of mass which is offset in a radial direction from the longitudinal axis of the coil and the lumen of the drive shaft. In another preferred embodiment, the abrasive element has a centre of mass which lies on the longitudinal axis of the coil and the lumen of the drive shaft.

The fluid impermeable membrane preferably extends around and is bonded to a surface of the torque transmitting coil proximal to the distal fluid inflatable support element.

The wall of the distal fluid inflatable support element preferably extends around the torque transmitting coil of the drive shaft.

In one preferred embodiment, the wall of the distal fluid inflatable support element is bonded to a segment of the circumference of the torque transmitting coil, a middle point of said segment being spaced from the longitudinal axis of the coil and the lumen of the drive shaft in the same direction as the centre of mass of the abrasive element.

The torque transmitting coil preferably comprises at least one space which separates individual windings of the coil, said space allowing fluid communication between the lumen of the drive shaft and the distal fluid inflatable support element.

One preferred embodiment comprises an anchoring sleeve underlying the fluid impermeable membrane along at least a distal end portion of the drive shaft, the fluid impermeable membrane being attached to said anchoring sleeve proximal to the distal fluid inflatable support element.

In one preferred embodiment, the torque transmitting coil has proximal and distal ends and the anchoring sleeve is disposed around at least a distal end portion of the torque transmitting coil.

Preferably, the torque transmitting coil has proximal and distal ends and the anchoring sleeve extends distally from the distal end of the coil such that the distal fluid inflatable support element formed around the anchoring sleeve from the fluid impermeable membrane is spaced away from the distal end of the torque transmitting coil and disposed (located) around at least a portion of the circumference of the anchoring sleeve.

The anchoring sleeve may extend proximally within and line the torque transmitting coil.

In a preferred embodiment, the drive shaft comprises inner and outer torque transmitting coils, the anchoring sleeve being sandwiched between said inner and outer torque transmitting coils, the anchoring sleeve and the inner torque transmitting coil extending distally from the distal end of the outer torque transmitting coil, the abrasive element being located around at least a portion of the circumference of the anchoring sleeve and being spaced away from the distal end of the outer torque transmitting coil.

In one embodiment, the anchoring sleeve may be closed at its distal end.

In one embodiment, the anchoring sleeve may have an opening therein associated with the distal fluid inflatable support element to allow pressurised fluid to flow through said opening into the distal fluid inflatable support element from the lumen of the drive shaft.

The distal end of the device may be closed by the fluid impermeable membrane and spaced in a longitudinal direction from the closed distal end of the anchoring sleeve to form a soft atraumatic cushion at the distal end of the device.

One preferred embodiment of the invention may comprise an elongate core element advanceable through the lumen of the drive shaft to stiffen the drive shaft and thereby assist in the advancement of the drive shaft along the vessel towards the treatment site.

The elongate core element may have a distal end configured for operational engagement with the distal end of the anchoring sleeve.

The elongate core element may be configured to be removed from the device after the distal end of the device has been advanced to the treatment site so that a detachable fluid supply tube can be attached to the device.

In one preferred embodiment, the elongate core element includes a lumen for the passage of fluid therealong, the elongate core element preferably having at least one opening located at or proximal to its distal end, said opening providing fluid communication between the lumen of the elongate core element and the lumen of the drive shaft.

The elongate core element may have a coil at its distal end, and the elongate core element may be a coil.

Preferably, the anchoring sleeve is formed from a fluid impermeable membrane.

The anchoring sleeve may comprise at least one opening located proximal to the closed distal end of the sleeve, said opening providing fluid communication between the lumen of the drive shaft and the distal fluid inflatable support element.

In a preferred embodiment, the device comprises a proximal fluid inflatable support element located proximal to and spaced away from the abrasive element, the proximal fluid inflatable support element having an outer wall.

In one preferred embodiment, the outer wall of the proximal fluid inflatable support element is continuous and integral with the fluid impermeable membrane.

The wall of the proximal fluid inflatable support element may be bonded to a segment of the circumference of the torque transmitting coil, a middle point of said segment being spaced from the longitudinal axis of the drive shaft in the same direction as the centre of mass of the abrasive element.

The torque transmitting coil may comprise at least one space which separates individual windings of the coil, said space allowing fluid communication between the lumen of the drive shaft and the proximal fluid inflatable support element.

The anchoring sleeve may have an opening therein associated with the proximal fluid inflatable support element to allow pressurised fluid to flow through said opening into the proximal fluid inflatable support element from the lumen of the drive shaft.

In one preferred embodiment, all of the pressurised fluid which flows through the lumen of the drive shaft exits from the device into the vessel through opening(s) in the wall(s) of the fluid inflatable support elements.

The distal fluid inflatable support element may have, when inflated, a centre of mass which is offset in a radial direction from the longitudinal axis of the torque transmitting coil and the lumen of the drive shaft.

The centre of mass of the distal fluid inflatable support element and the centre of mass of the abrasive element may be offset from the longitudinal axis of the torque transmitting coil and the lumen of the drive shaft in diametrically opposite directions.

In one preferred embodiment, the wall of the distal fluid inflatable support element defines a fluid inflatable space that extends only partially around a circumference of the torque transmitting coil so that, when the distal inflatable support element is fluid inflated, its centre of mass is offset from a longitudinal axis of the torque transmitting coil and the lumen of the drive shaft in one direction, the distal fluid inflated support element acting, during rotation of the drive shaft, as a counterweight to the abrasive element which has its centre of mass offset from the longitudinal axis of the torque transmitting coil and the lumen of the drive shaft in the opposite direction.

In one preferred embodiment, the wall of the distal fluid inflatable support element defines a fluid inflatable space that extends only partially around a circumference of the anchoring sleeve so that, when the distal inflatable support element is fluid inflated, its centre of mass is offset from a longitudinal axis of the torque transmitting coil and the lumen of the drive shaft in one direction, the distal fluid inflated support element acting, during rotation of the drive shaft, as a counterweight to the abrasive element which has its centre of mass offset from the longitudinal axis of the torque transmitting coil and the lumen of the drive shaft in the opposite direction.

The proximal fluid inflatable support element may have, when inflated, a centre of mass which is offset in a radial direction from the longitudinal axis of the torque transmitting coil and the lumen of the drive shaft.

The centre of mass of the proximal fluid inflatable support element and the centre of mass of the abrasive element may be offset from the longitudinal axis of the torque transmitting coil and the lumen of the drive shaft in diametrically opposite directions.

In one preferred embodiment, the wall of the proximal fluid inflatable support element defines a fluid inflatable space that extends only partially around a circumference of the torque transmitting coil so that, when the proximal inflatable support element is fluid inflated, its centre of mass is offset from a longitudinal axis of the torque transmitting coil and the lumen of the drive shaft in one direction, the distal fluid inflated support element acting, during rotation of the drive shaft, as a counterweight to the abrasive element which has its centre of mass offset from the longitudinal axis of the torque transmitting coil and the lumen of the drive shaft in the opposite direction.

In another preferred embodiment, fluid inflatable spaces within both the distal and proximal fluid inflatable support elements extend radially away from the longitudinal axis of the torque transmitting coil and the lumen of the drive shaft in a direction diametrically opposite to the direction in which the center of mass of the abrasive element is spaced away from the longitudinal axis of the torque transmitting coil and the lumen of the drive shaft.

In another preferred embodiment, the distal fluid inflatable support element may have, when inflated, a centre of mass which lies along the longitudinal axis of the torque transmitting coil and the lumen of the drive shaft.

Preferably, in this preferred embodiment, a fluid inflatable space within the distal fluid inflatable support element extends uniformly around an entire circumference of the drive shaft, providing the distal support element with a centre of mass which lies along the longitudinal axis of the torque transmitting coil and the lumen of the drive shaft when said distal support element is fluid inflated.

The proximal fluid inflatable support element may also have, when inflated, a centre of mass which lies along the longitudinal axis of the torque transmitting coil and the lumen of the drive shaft.

In a preferred embodiment, a fluid inflatable space within the proximal fluid inflatable support element extends uniformly around a longitudinal axis of the torque transmitting coil and the lumen of the drive shaft, therefore providing a fluid inflated proximal support element with a centre of mass which lies along the longitudinal axis of the torque transmitting coil and the lumen of the drive shaft when the proximal support element is fluid inflated.

In a preferred embodiment, the wall of the distal fluid inflatable support element has an outflow opening located such that said outflow opening, during rotation of the drive shaft, faces an inner surface of a treated vessel so that fluid flowing through the outflow opening forms a layer of fluid between the outer wall of the rotating fluid inflated distal support element and a wall of the treated vessel, said layer of fluid forming a fluid bearing between the outer wall of the rotating fluid inflated distal support element and the wall of the treated vessel.

In a preferred embodiment, at least a few openings in the outer wall of a rotating fluid inflated distal support element are located around circumference of the wall of the inflated distal support element such that at any time during rotation of the drive shaft at least one of said few openings is facing an inner surface of a treated vessel, so that a flow of fluid through the opening forms a layer of fluid between the wall of the rotating fluid inflated distal support element and a wall of the treated vessel, said layer of fluid forming a fluid bearing between the wall of the rotating fluid inflated support element and the wall of the treated vessel.

In a preferred embodiment, at least one opening in the wall of a rotating fluid inflated proximal support element is located such that at any time during rotation of the drive shaft said opening is facing an inner surface of a treated vessel, so that a flow of fluid through the opening forms a layer of fluid between the wall of the rotating fluid inflated proximal support element and a wall of the treated vessel, said layer of fluid forming a fluid bearing between the wall of the rotating fluid inflated proximal support element and the wall of the treated vessel.

There may be a plurality of openings in the wall of the fluid inflatable proximal support element, said openings being located around the circumference of the wall of the fluid inflatable proximal support element such that, during rotation of the drive shaft, at least some of said openings face an inner surface of a treated vessel, so that flows of fluid through the openings form a layer of fluid between the outer wall of the fluid inflated proximal support element and a wall of the treated vessel, said layer of fluid forming a fluid bearing between the outer wall of the rotating fluid inflated proximal support element and the wall of the treated vessel.

In one preferred embodiment, there is a plurality of openings in the wall of the fluid inflatable distal support element, said openings being located around the circumference of the wall of the fluid inflatable distal support element such that, during rotation of the drive shaft, at least some of said openings face an inner surface of a treated vessel, so that flows of fluid through the openings form a layer of fluid between the outer wall of the fluid inflated distal support element and a wall of the treated vessel, said layer of fluid forming a fluid bearing between the outer wall of the rotating fluid inflated distal support element and the wall of the treated vessel.

The walls of both inflatable support elements may be made from a continuous stretchable membrane, said fluid impermeable stretchable membrane being sandwiched between the torque transmitting coil and at least one non-stretchable sleeve, the non-stretchable sleeve being disposed around the stretchable membrane between the fluid inflatable support elements. This non-stretchable sleeve may be formed in two sections, each section being disposed on either side of the abrasive element.

A second long, non-stretchable sleeve preferably overlaps the stretchable membrane for a short distance proximal to the proximal fluid inflatable support element and extends in a proximal direction around the torque transmitting coil towards the proximal end of the drive shaft. This non-stretchable sleeve is preferably fluid impermeable.

An anchoring sleeve may be disposed around the torque transmitting coil at least along a length of the drive shaft occupied by fluid inflatable support elements, said anchoring sleeve being disposed over the coil under the fluid impermeable membrane which forms the distal fluid inflatable support element, the fluid impermeable membrane along a length of the fluid inflatable support elements being bonded to the anchoring sleeve only along one side of a circumference of the drive shaft, thereby preventing the fluid inflatable support elements from expanding uniformly around an entire circumference of the anchoring sleeve when fluid inflated so as to form a fluid inflated counterweights with centers of mass spaced radially away from a longitudinal axis of the torque transmitting coil and the lumen of the drive shaft in a direction opposite to the direction in which a centre of mass of the abrasive element is spaced away from the longitudinal axis of the torque transmitting coil and the lumen of the drive shaft.

The lumen of the drive shaft may have proximal and distal portions, the proximal portion of the the lumen having a larger cross-sectional area relative to the cross-sectional area of the distal portion of the lumen so that per unit of length hydraulic resistance to fluid flow of the proximal portion of the lumen is less than the hydraulic resistance to fluid flow of the distal portion of the lumen.

Reference is made to "distal" and "proximal" ends and to flow of fluid in an "antegrade" and "retrograde" direction. For the avoidance of doubt, and for the purpose of this specification, the distal end is considered to refer to the end of the device which is inserted into the vessel in the body of the patient and the proximal end is the end of the device which remains outside the body of the patient and is connected to an advancing and rotational drive assembly. The term 'antegrade flow' refers to a direction of fluid flow from the proximal to the distal end of the device.

Similarly, the term 'retrograde flow' refers to a fluid flow in the opposite direction, i.e. from the distal to the proximal end of the device. The antegrade flowing fluid is indicated by arrows 'FF' in the drawings. The retrograde flowing fluid is indicated by arrows 'RF' in the drawings. Embolic particles are marked as 'EP' in the drawings.

BRIEF DESCRIPTION OF THE DRAWINGS

Embodiments of the invention will now be described, by way of example only, with reference to the accompanying drawings, in which:

FIG. 1 is a longitudinal cross-sectional view of a distal end portion of a rotational atherectomy device according to a first embodiment of the invention. The device comprises a rotatable drive shaft, an abrasive element mounted to the drive shaft proximal to its distal end and, a pair of fluid inflatable support elements. The fluid inflatable support elements are located distal and proximal to the abrasive element. The abrasive element and the fluid inflatable support elements are rotatable together with the drive shaft. The drive shaft comprises a torque transmitting coil and a long lumen having a fluid impermeable wall and configured for transfer of pressurized fluid towards the distal end of the drive shaft. The long lumen of the drive shaft is coaxial with the torque transmitting coil and is in fluid communication with both fluid inflatable support elements. The distal fluid inflatable support element is formed from a fluid impermeable membrane that crosses a longitudinal axis of the lumen of the drive shaft (and of the torque transmitting coil) at a distal end of the device.

FIG. 2 shows the device of FIG. 1 after the flow of pressurized fluid along the lumen the drive shaft has been initiated and the support elements have been inflated by said flow of pressurized fluid. FIG. 2 illustrates that the fluid impermeable membrane prevents pressurized fluid flowing along the lumen of the drive shaft from entering the vessel in the direction of the longitudinal axis of the lumen (and the coil). FIG. 2 illustrates that the pressurized fluid has to pass through the fluid inflatable support elements and inflate them. The pressurized fluid exits from the device through outflow openings in the fluid inflated support elements. The pressurized fluid exits through the outflow openings in directions which are different from the direction of the longitudinal axis of the coil and the lumen.

FIG. 6 illustrates that a fluid inflatable space within the distal support elements extends only partially around a circumference of the torque transmitting coil;

FIG. 8 illustrates that a fluid inflatable space within the proximal support elements extends only partially around a circumference of the torque transmitting coil;

FIG. 9 is a longitudinal cross-sectional view of a distal end portion of a rotational atherectomy device according to a second embodiment of the invention, the device comprising an anchoring sleeve which is underlying the fluid impermeable membrane along a distal end portion of the torque transmitting coil. The walls of the fluid inflatable support elements are bonded only to segments of the circumference of the anchoring sleeve, said segments of the anchoring sleeve being located such that a middle point of each segment is spaced from the longitudinal axis of the torque transmitting coil in the same direction as a centre of a mass of the abrasive element. The abrasive element extends around the anchoring sleeve and has a center of mass spaced away from the longitudinal axis of the drive shaft;

FIG. 10 shows the device of FIG. 9 after the flow of pressurized fluid along the lumen the drive shaft has been initiated. FIG. 10 illustrates that the pattern of fluid flow through the device is similar to that shown in FIG. 2 of the first embodiment. The support elements are inflated by the pressurized fluid that flows into the inflatable support elements through apertures in the anchoring sleeve.

FIG. 11 shows the first modification in which the abrasive element is bonded by a longitudinally extending strap to the outer surface of the fluid impermeable membrane. In the modified embodiment of FIG. 11, the fluid impermeable membrane forms the walls of both fluid inflatable support elements, but does not extend around a proximal end portion of the torque transmitting coil. The anchoring sleeve extends proximally around the torque transmitting coil towards the proximal end of the drive shaft. The anchoring sleeve forms the wall of the lumen of the drive shaft and therefore should be made from a fluid impermeable material.

FIG. 12 illustrates that the pattern of fluid flow through the device is similar to that shown in FIG. 2 of the first embodiment.

FIG. 16 illustrates that a fluid inflatable space within the distal support elements extends only partially around a circumference of the anchoring sleeve;

FIG. 18 illustrates that a fluid inflatable space within the proximal support elements extends only partially around a circumference of the anchoring sleeve
FIG. 19 shows a second modification of the second embodiment of the device of the invention.
FIG. 19 shows the device which is similar to the device shown in FIG. 11, but in which the anchoring sleeve extends only around a distal end portion of the the torque transmitting coil. The fluid impermeable membrane forms walls of the inflatable support elements around the distal end potion of the torque transmitting coil and extends in a proximal direction around the torque transmitting coil towards the proximal end of the drive shaft;

FIG. 20 shows the device of FIG. 19 after an antegrade flow of fluid has been initiated. FIG. 20 illustrates that the pattern of fluid flow through the device is similar to that shown in FIG. 2 of the first embodiment and FIG. 12 of the first modification of the second embodiment;

FIG. 21 shows a third modification of the second embodiment of the device of the invention. FIG. 21 shows the device which is similar to the device shown in FIG. 11, but in which the anchoring sleeve is closed at its distal end. The device shown in FIG. 21 also differs from the device shown in FIG. 11 in that the closed distal end of the anchoring sleeve is spaced in the longitudinal direction from the distal end of the device, the distal end of the device being closed by the membrane so that the space between the closed end of the anchoring sleeve and the closed end of the device form a soft atraumatic cushion at the distal end of the device. The device shown in FIG. 21 also differs from the device shown in FIG. 11 in that the anchoring sleeve extends distally from a distal end of the torque transmitting coil such that the inflatable support elements are spaced away from the distal end of the torque transmitting coil. Yet another difference between the second and third modifications of the second embodiment is that the abrasive element shown in FIG. 21 is attached to the membrane by a flexible strap which extends around the membrane in FIG. 21 and not along it as shown in FIG. 11;

FIG. 22 shows the device of FIG. 21 after an antegrade flow of pressurized fluid through the device has been initiated. The support elements are inflated by the pressurized fluid that flows into the inflatable support elements through apertures in the anchoring sleeve. FIG. 22 illustrates that the pattern of fluid flow through the device is similar to that shown in FIG. 2 of the first embodiment and FIGS. 12 and 20 of the first and second modifications of the second embodiment;

FIG. 23 shows a fourth modification of the second embodiment of the device of the invention. The fourth modification of FIG. 23 is similar to the third modification of the second embodiment of FIG. 21, but differs in that the centres of mass of the inflatable support elements are laying along the longitudinal axis of the torque transmitting coil and of the lumen of the drive shaft;

FIG. 24 shows the device of FIG. 23 after an antegrade flow of fluid has been initiated and the support elements have been inflated. FIG. 24 illustrates that fluid inflatable spaces within the support elements extend uniformly around the longitudinal axis of the torque transmitting coil and the lumen of the drive shaft, therefore providing the fluid inflated support elements with centers of mass which are laying along the longitudinal axis of the torque transmitting coil and the lumen of the drive shaft, when the support elements are fluid inflated. FIG. 24 illustrates that the pattern of fluid flow through the device is similar to that shown in FIG. 2 of the first embodiment and FIGS. 12, 20 and 22 of the first, second and third modifications of the second embodiment. The pressurized fluid is exiting from the device through the outflow openings located around the entire circumference of the inflated support elements;

FIG. 25 shows a fifth modification of the second embodiment of the device of the invention. The embodiment of FIG. 25 is similar to the fourth modification of the second embodiment shown in FIG. 23, but differs in that the drive shaft comprises inner and outer torque transmitting coils. The anchoring sleeve is sandwiched between the inner and outer torque transmitting coils. The anchoring sleeve and the inner torque transmitting coil extend distally from the distal end of the outer torque transmitting coil such that the inflatable support elements formed around the anchoring sleeve from the fluid impermeable membrane are spaced away from the distal end of the outer torque transmitting coil;

FIG. 26 shows the device of FIG. 25 after an antegrade flow of fluid has been initiated and the support elements have been inflated. FIG. 26 illustrates that the pattern of fluid flow through the device is similar to that shown in FIG. 24 of the fourth modification of the second embodiment;

FIG. 27 is a side sectional view of a portion of a blood vessel having a stenotic lesion. FIG. 27 illustrates the rotational device of a sixth modification of the second embodiment of the invention which has been advanced across the stenotic lesion to a position in which the distal fluid inflatable support element is located distal to the stenotic lesion and the proximal fluid inflatable support element is intentionally located proximal to the stenotic lesion to be treated. The device of FIG. 27 is similar to the device of the third modification of the second embodiment of FIG. 21, but differs in that it comprises an elongate core element disposed in the lumen of the drive shaft to stiffen the drive shaft and thereby assist in the advancement of the device along the vessel towards and across the stenotic lesion;

FIG. 28 shows the same view as FIG. 27 but with the core element being partially withdrawn from the lumen of the drive shaft;

FIG. 29 shows the same view as FIGS. 27 and 28, but with the core element completely removed from the lumen of the drive shaft. It should be noted that the core element should be removed completely from the rest of the device to allow attachment of a detachable fluid supply tube to the device;

FIG. 30 shows the same view as FIG. 29 but after a flow of pressurized fluid has been initiated in an antegrade direction along the lumen of the drive shaft and through the openings in the anchoring sleeve into the inflatable support elements to inflate said support elements. The pressurized fluid flowing along the lumen of the drive shaft is entering the treated vessel only through the openings in the walls of the inflatable support elements;

FIGS. 31 through 36 illustrate abrading of the stenotic lesion by the rotating abrasive element and formation of fluid bearings between the inner surface of the vessel and the walls of the rotating fluid inflated support elements, said fluid bearings being formed by flow of fluid through the openings in the walls of the fluid inflated support elements;

FIG. 37 shows the distal end section of the device after rotation of the device has been stopped but prior to stopping the flow of pressurized fluid along the lumen of the drive shaft.

FIG. 38 shows the distal end portion of the device after the flow of pressurized fluid along the lumen of the drive shaft has been stopped;

FIGS. 39 and 40 illustrate the removal of the device from the treated vessel and appearance of the treated vessel after removal of the device;

FIG. 41 is similar to the device shown in FIG. 27, but differs in that the core element comprises a long lumen, said lumen being in fluid communication with the lumen of the drive shaft through an opening located in a wall of the core element adjacent to its distal end;

FIG. 42 shows the device of FIG. 41 in which pressurized fluid is flowing from the lumen of the core element into the lumen of the drive shaft;

FIG. 43 shows the device of FIG. 42 in which the core element is being withdrawn from the lumen of the drive shaft and the device. The continuous flow of the pressurized fluid from the lumen of the core element into the lumen of the drive shaft is assisting in removing the core element from the lumen of the drive shaft without changing position of the device in the treated vessel;

FIG. 44 shows the device of FIGS. 42 and 43 except that the pressurized fluid has been pumped from the lumen of the core element into the lumen of the drive shaft at such a combination of fluid pressure and fluid flow rates which caused the distal inflatable support element (counterweight) to become sufficiently distended to become anchored distal to or against the stenotic lesion to be treated.

FIG. 45 shows that the anchoring the distal fluid inflatable support element either distal to or against the stenotic lesion to be treated may help in removing the core element from the lumen of the drive shaft without changing the position of the device in the vessel to be treated.

FIG. 46 shows a longitudinal cross-sectional view of a distal end portion of a third embodiment of the device of the invention. In this embodiment the inflatable support elements are formed from a fluid impermeable stretchable membrane. The stretchable membrane proximal to the distal fluid inflatable support element is sandwiched between the torque transmitting coil and a non-stretchable sleeve. Another non-stretchable, fluid impermeable sleeve extends around a proximal end portion of the stretchable membrane and further around the torque transmitting coil towards the proximal end of the drive shaft;

FIG. 47 shows one modification of the third embodiment of the device of the invention. This embodiment is similar to that shown in FIG. 44, but differs in that the non-stretchable sleeve is comprised of two segments, one segment being disposed around the stretchable membrane between the abrasive element and the distal fluid inflatable support element and the other between the abrasive element and the proximal fluid inflatable support element;

FIG. 48 shows the device of FIG. 47 after an antegrade flow of fluid has been initiated and the support elements have been inflated. FIG. 48 illustrates that the pattern of fluid flow through the device is similar to that shown in FIG. 26 of the fifth modification of the second embodiment;

FIG. 49 shows the device after the antegrade flow of pressurized fluid has been initiated and the support elements have been inflated. The device of FIG. 49 is similar to the device of the third modification of the second embodiment of the device shown in FIG. 22, but differs in that the lumen of the drive shaft has proximal and distal portions. The proximal portion of the the lumen has a larger cross-sectional area relative to the cross-sectional area of the distal portion of the lumen so that, per unit of length, hydraulic resistance to fluid flow of the proximal portion of the lumen is less than the hydraulic resistance to fluid flow of the distal portion of the lumen.

DETAILED DESCRIPTION

Figure 5:
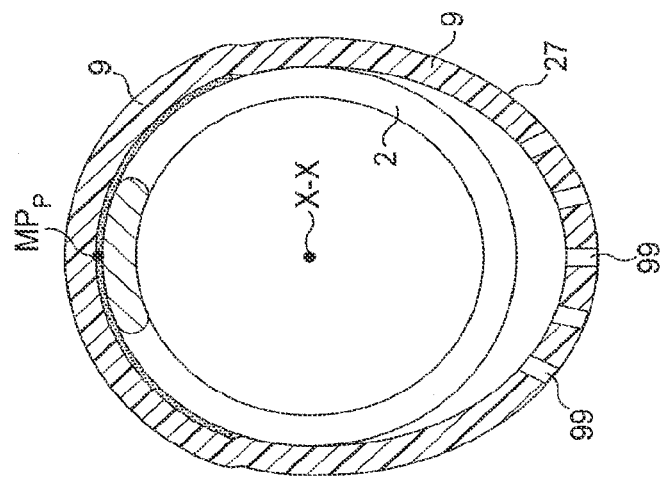
FIG. 5 shows a cross-section through $A1^{111}$-$A1^{111}$ of FIG. 1.
Figure 4:
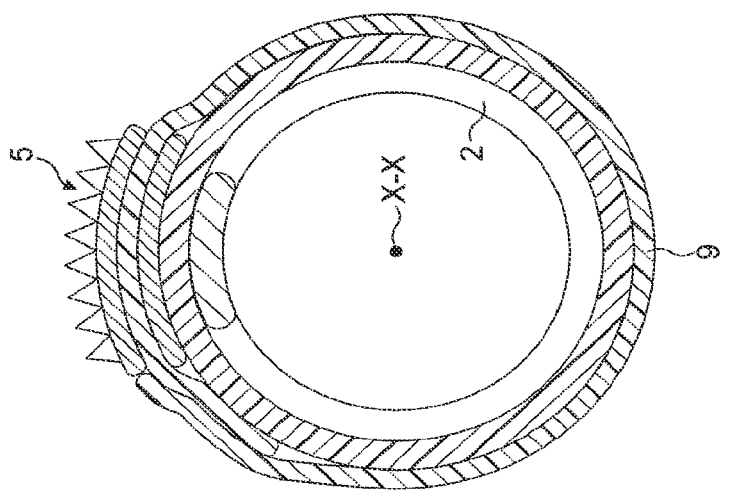
FIG. 4 shows a cross-section through $A1^{11}$-$A1^{11}$ of FIG. 1.
Figure 3:
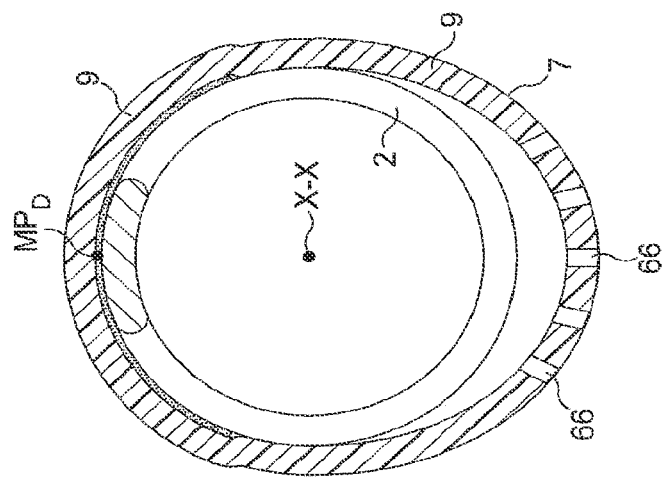
FIG. 3 shows a cross-section through $A1^1$-$A1^1$ of FIG. 1.

In FIGS. 1 to 49, the direction of movement of the atherectomy device is indicated by arrow marked "DM", flow of fluid in an antegrade direction through the atherectomy device is indicated by arrows "FF" and flow of fluid around the device and across a stenotic lesion in a retrograde direction is indicated by arrows marked "RF". Embolic particles abraded from the stenotic lesion are indicated as "EP". Embolic particles EP abraded from the stenotic lesion are entrained by the retrograde flowing fluid RF and aspirated into a drainage lumen formed between the rotatable drive shaft and a stationary drive shaft sheath 900. Alternatively, embolic particles EP may be aspirated into a drainage lumen of a separate drainage catheter (not shown). Embolic particles EP are removed from the treated vessel and out of the patient's body.

FIGS. 1 through 8 illustrate in longitudinal and transverse cross-sections a distal end portion of the first embodiment of the rotational atherectomy device of the invention. The rotational atherectomy device is comprised of a rotatable, flexible drive shaft 1, a distal fluid inflatable support element 3 located at a distal end 4 of the device and an abrasive element 5 mounted to the drive shaft 1 proximal to and spaced away from the distal fluid inflatable support element 3. The drive shaft 1 comprises a torque transmitting coil 2. The abrasive element 5 and the distal fluid inflatable support element 3 are rotatable together with the drive shaft 1. The drive shaft 1 includes a long lumen 6 for the transport of pressurized fluid to the distal fluid inflatable support element 3. In FIGS. 1 to 8, a wall 7 of the distal fluid inflatable support element 3 and a wall 8 of the long lumen 6 of the drive shaft 1 are formed from a single fluid impermeable membrane 9. The fluid impermeable membrane 9 extends around the torque transmitting coil 2. The torque transmitting coil 2, the long lumen 6 of the drive shaft 1 and the drive shaft 1 itself have common longitudinal axis X-X. The fluid impermeable membrane 9 crosses the longitudinal axis X-X at the distal end 4 of the device, thereby preventing pressurized fluid flowing along the lumen 6 of the drive shaft 1 from entering the treated vessel in the direction of said longitudinal axis X-X. Therefore, the pressurized fluid has to pass through and inflate the distal fluid inflatable support element 3, prior to exiting from the device through outflow openings 66 in the distal fluid inflatable support element 3 in a direction different from the direction of the longitudinal axis X-X of the torque transmitting coil 2 and the lumen 6 of the drive shaft 1.

Preferably, the device comprises a proximal fluid inflatable support element 23 located proximal to and spaced away from the abrasive element 5. FIGS. 1 and 2 illustrate that a wall 27 of the proximal fluid inflatable support element 23 is continuous and integral with the fluid impermeable membrane 9 which forms the wall 7 of the distal fluid inflatable support element 3. FIG. 2 also illustrates that the pressurized fluid is passing through and inflating the proximal fluid inflatable support element 23, prior to exiting from the device through outflow openings 99 in the proximal fluid inflatable support element 23.

Figure 7:
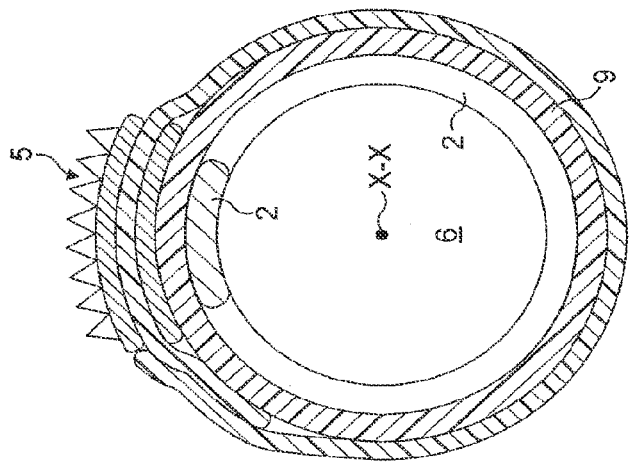
FIG. 7 shows a cross-section through $A3^{11}$-$A3^{11}$ of FIG. 2.
Figure 6:
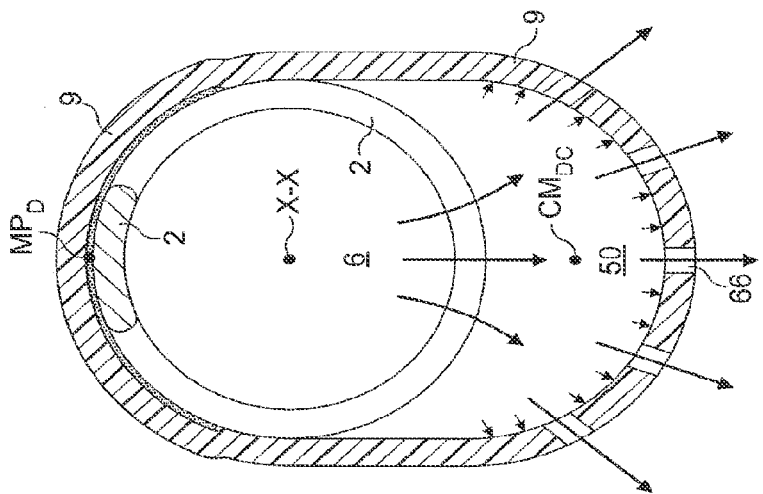
FIG. 6 shows a cross-section through $A3^1$-$A3^1$ of FIG. 2.
Figure 11:
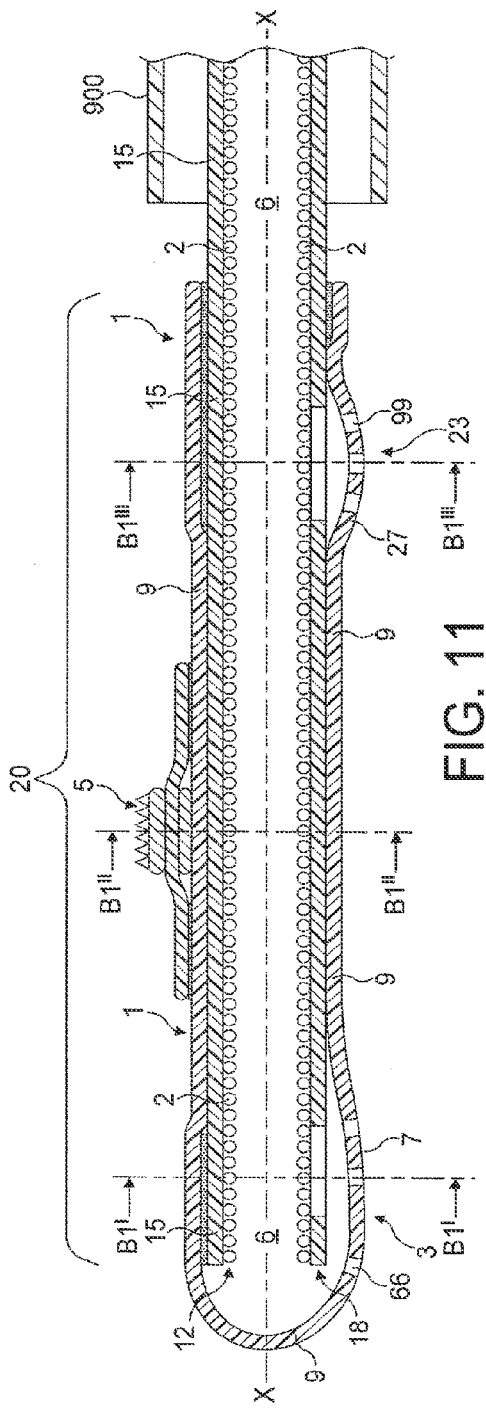
FIG. 11 shows a longitudinal cross-sectional view of a distal end portion of a first modification of the second embodiment of the invention.
Figure 12:
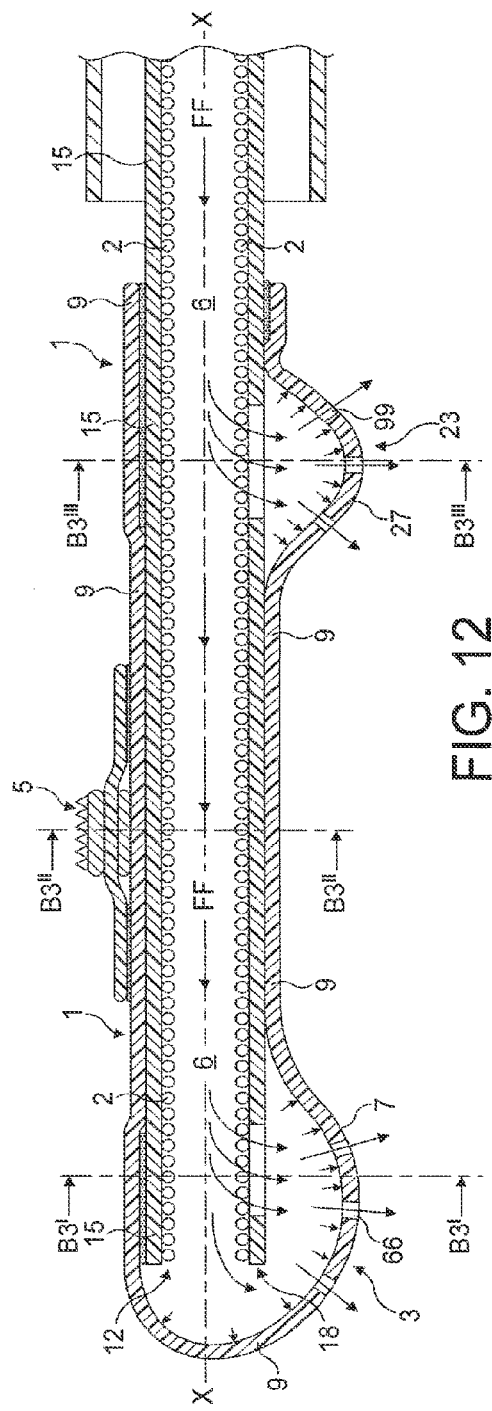
FIG. 12 shows the device of FIG. 11 after the flow of pressurized fluid along the lumen the drive shaft has been initiated.
Figure 15:
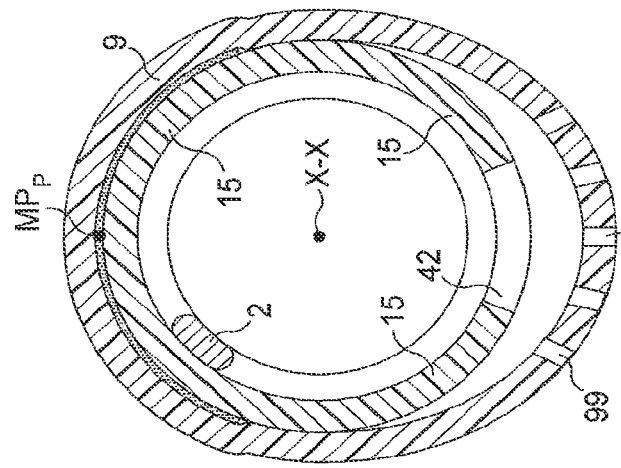
FIG. 15 shows a cross-section through $B1^{111}$-$B1^{111}$ of FIG. 11.
Figure 14:
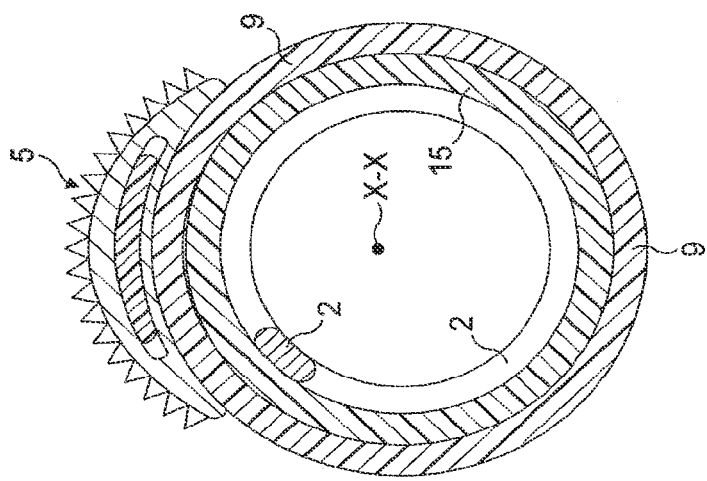
FIG. 14 shows a cross-section through $B1^{11}$-$B1^{11}$ of FIG. 11.
Figure 13:
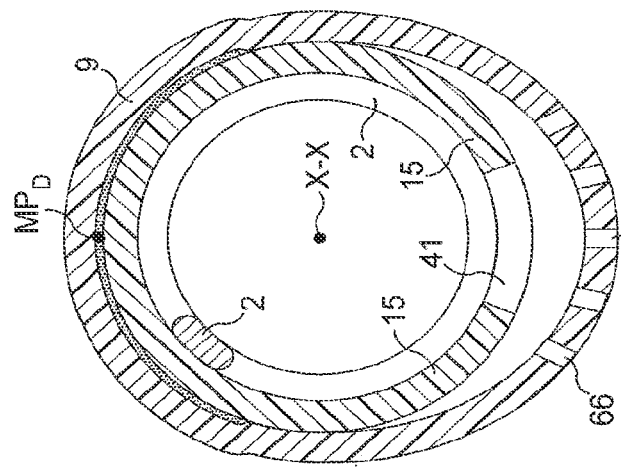
FIG. 13 shows a cross-section through $B1^1$-$B1^1$ of FIG. 11.
Figure 18:
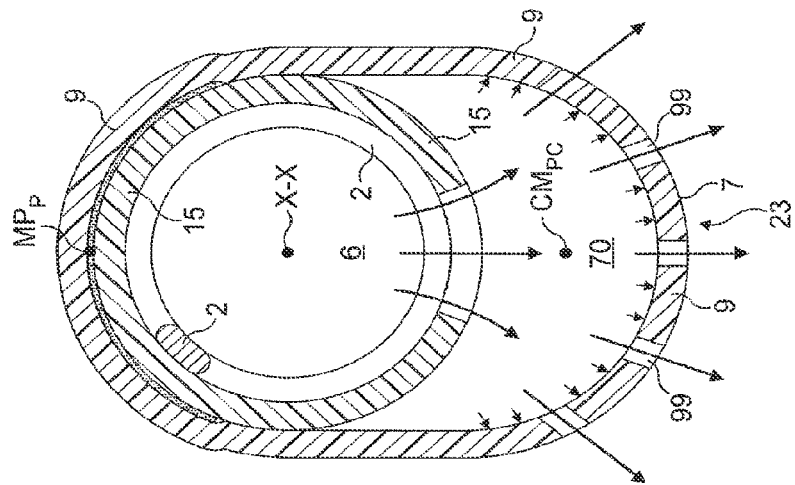
FIG. 18 shows a cross-section through $B3^{111}$-$B3^{111}$ of FIG. 12.
Figure 17:
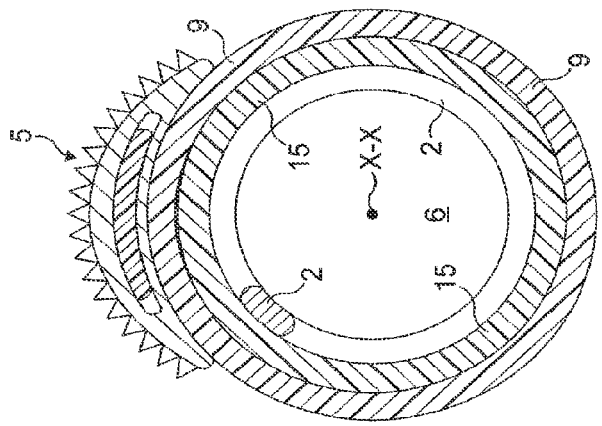
FIG. 17 shows a cross-section through $B3^{11}$-$B3^{11}$ of FIG. 12.
Figure 16:
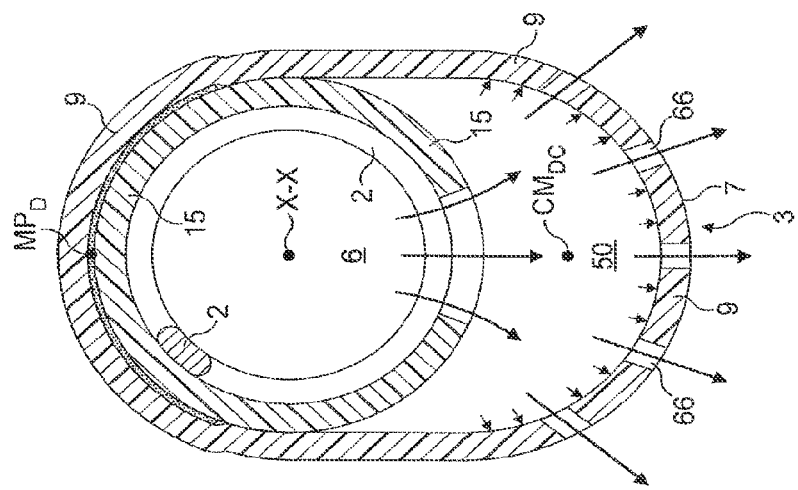
FIG. 16 shows a cross-section through $B3^1$-$B3^1$ of FIG. 12.
Figure 31:
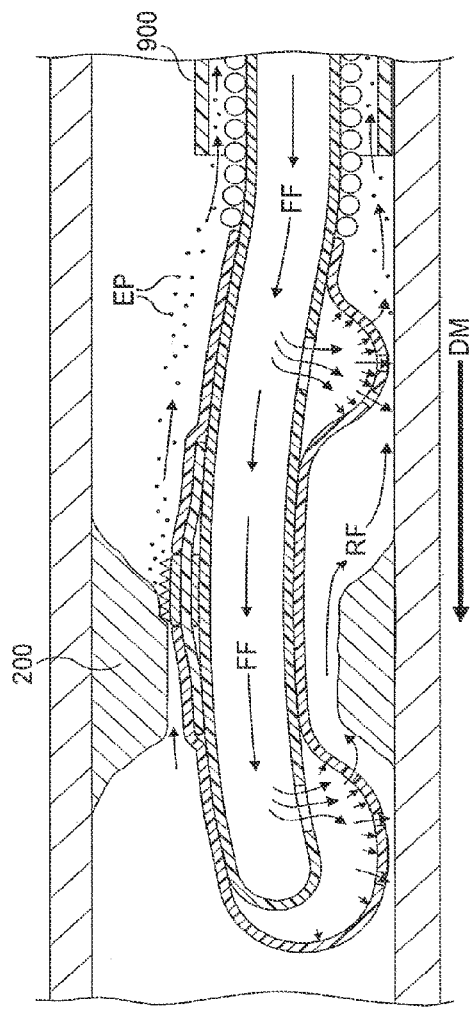
Figure 32:
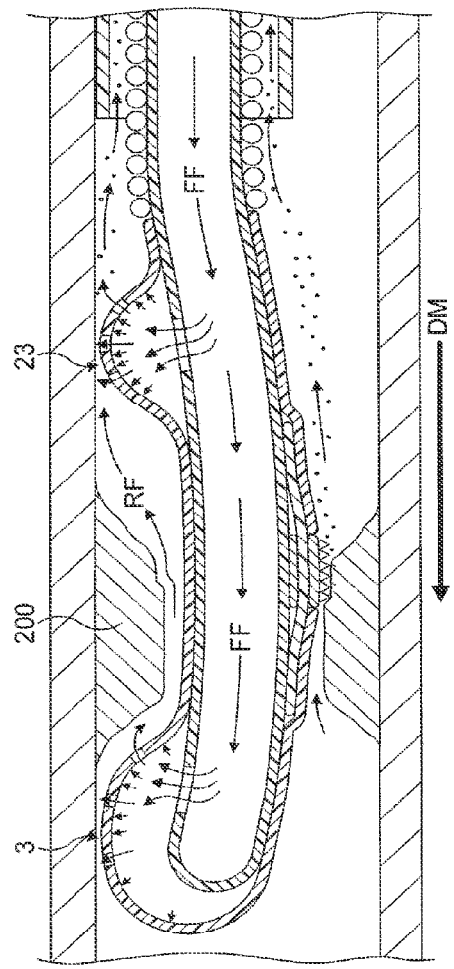
Figure 33:
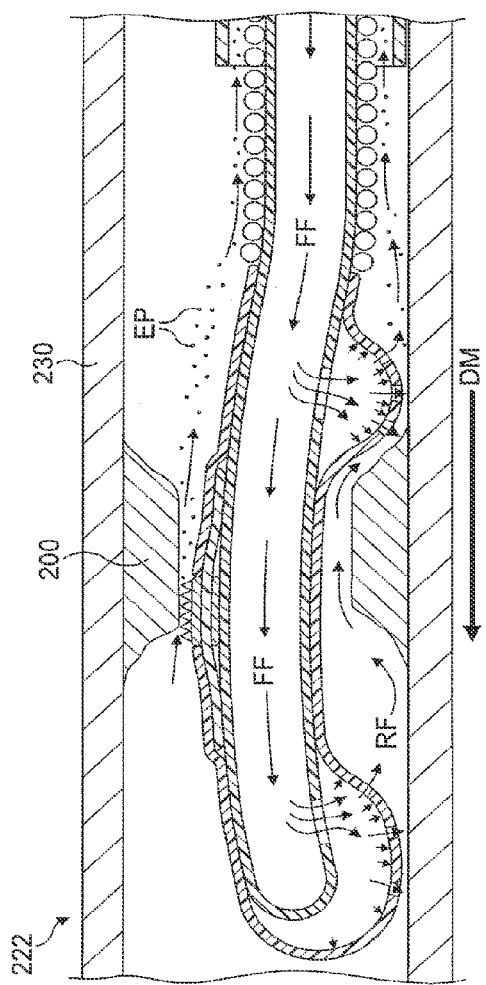
Figure 34:
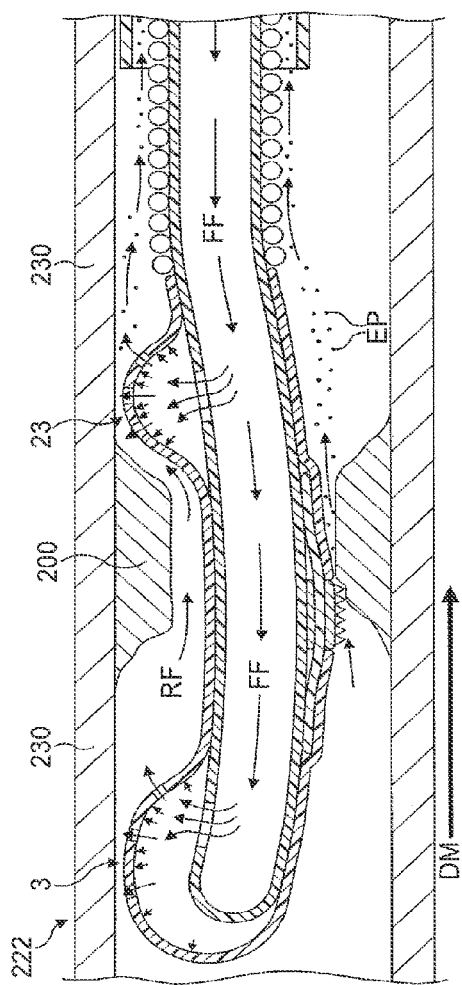

FIGS. 2, 6 and 7 illustrate best that the wall 7 of the distal fluid inflatable support element 3 is bonded only to a segment of the circumference of the torque transmitting coil 2, said segment of the coil 2 being located such that a middle point $MP_D$ of the segment is spaced from the longitudinal axis X-X of the torque transmitting coil 2 in the same direction as a centre of a mass of the abrasive element 5.

Figure 8:
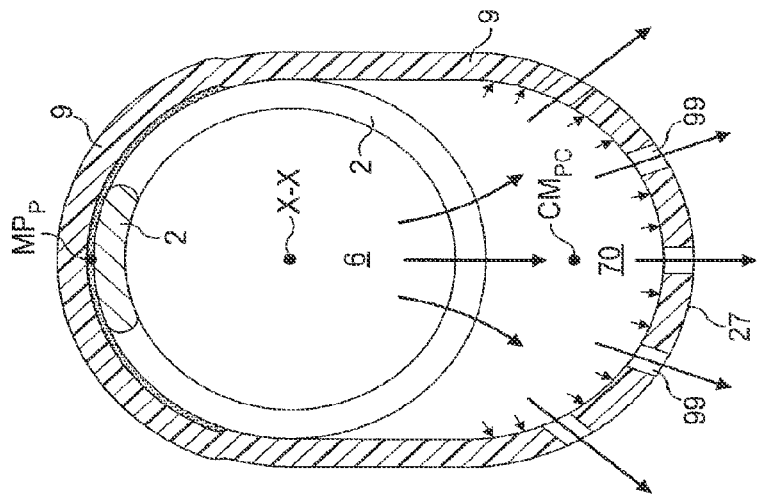
FIG. 8 shows a cross-section through $A3^{111}$-$A3^{111}$ of FIG. 2.

FIGS. 2, 7 and 8 illustrate best that the wall 27 of the proximal fluid inflatable support element 23 is also bonded only to a segment of the circumference of the torque transmitting coil 2, said segment of the coil 2 being located such that a middle point $MP_P$ of the segment is spaced from the longitudinal axis X-X of the torque transmitting coil 2 in the same direction as a centre of a mass of the abrasive element 5.

FIGS. 2 and 6 illustrate best that the wall 7 of the distal fluid inflatable support element 3 defines a fluid inflatable space 50 that extends only partially around the circumference of the torque transmitting coil 2 so that, when the distal inflatable support element 3 is fluid inflated, its centre of mass $CM_{DC}$ is offset from the longitudinal axis X-X of the torque transmitting coil 2 and the lumen 6 of the drive shaft 1 in one direction, the distal fluid inflated support element 3 acting, during rotation of the drive shaft 1, as a counterweight to the abrasive element 5 which has its centre of mass offset from the longitudinal axis X-X of the torque transmitting coil 2 and the lumen 6 of the drive shaft 1 in the opposite direction.

FIGS. 2 and 6 illustrate best that the wall 7 of the distal fluid inflatable support element 3 defines a fluid inflatable space 50 that extends only partially around the circumference the torque transmitting coil 2 so that, when the distal inflatable support element 3 is fluid inflated, its centre of mass $CM_{DC}$ is offset from the longitudinal axis X-X of the torque transmitting coil 2 and the lumen 6 of the drive shaft 1 in one direction, the distal fluid inflated support element 3 acting, during rotation of the drive shaft 1, as a counterweight to the abrasive element 5 which has its centre of mass offset from the longitudinal axis X-X of the torque transmitting coil 2 and the lumen 6 of the drive shaft 1 in the opposite direction.

FIGS. 2 and 8 illustrate best that the wall 27 of the proximal fluid inflatable support element 23 defines a fluid inflatable space 70 that extends only partially around the circumference the torque transmitting coil 2 so that, when the proximal inflatable support element 23 is fluid inflated, its centre of mass $CM_{PC}$ is offset from the longitudinal axis X-X of the torque transmitting coil 2 and the lumen 6 of the drive shaft 1 in one direction, the proximal fluid inflated support element 23 acting, during rotation of the drive shaft 1, as a counterweight to the abrasive element 5 which has its centre of mass offset from the longitudinal axis X-X of the torque transmitting coil 2 and the lumen 6 of the drive shaft 1 in the opposite direction.

FIGS. 9 to 20 illustrate an anchoring sleeve 15 which is open at its distal end 18. The anchoring sleeve 15 extends around the torque transmitting coil 2. The anchoring sleeve 15 is underlying the fluid impermeable membrane 9 along a distal end portion 20 of the drive shaft 1. FIGS. 9 to 20 illustrate that the open distal end 18 of the anchoring sleeve 15 coincides with the distal end 12 of the torque transmitting coil 2. It should be noted that the device may be constructed with the distal end 12 of the torque transmitting coil 2 positioned proximal to and spaced away from the distal end 18 of the anchoring sleeve 15.

FIGS. 9 and 10 illustrate that the fluid impermeable membrane 9 is attached or bonded to the anchoring sleeve 15 around its entire circumference proximal to the distal fluid inflatable support element 3. FIGS. 9 and 10 also illustrate the separate fluid impermeable membrane 29, which forms the wall 27' of the proximal fluid inflatable support element 23. The fluid impermeable membrane 29 is attached or bonded to the anchoring sleeve 15 around its entire circumference both distal and proximal to the proximal fluid inflatable support element 23.

FIGS. 11 to 18 illustrate the first modification of the second embodiment of the device in which the anchoring sleeve 15 extends in a proximal direction towards the proximal end of the drive shaft 1. The anchoring sleeve 15 forms the wall of the lumen 6 of the drive shaft 1 and therefore should be made from a fluid impermeable material.

FIGS. 19 and 20 illustrate a second modification of the second embodiment of the device in which the anchoring sleeve 15 extends around the torque transmitting coil 2 only along a distal end portion 20 of the drive shaft 1. The fluid impermeable membrane 9 extends from the distal end of the device towards the proximal end of the drive shaft 1. FIGS. 19 and 20 show that the fluid impermeable membrane 9 may alone form the wall of the lumen 6 of the drive shaft 1 proximal to a proximal end 30 of the anchoring sleeve 15.

FIGS. 1 to 20 illustrate the embodiments of the device in which the distal end of the drive shaft 1 coincides with the distal end 12 of the torque transmitting coil 2.

The proximal ends of the drive shaft 1 and the torque transmitting coil 2 are not shown in the drawings, but it should be noted that the torque transmitting coil 2 does not have to extend proximally along the entire length of the drive shaft 1.

FIGS. 21 to 48 illustrate embodiments of the device in which the anchoring sleeve 15' is closed at its distal end. In these exemplary embodiments, the distal end of the lumen 6 of the drive shaft 1 coincides with the distal end 18' of the anchoring sleeve 15'. In these embodiments, the closed distal end 18' of the anchoring sleeve 15' is spaced in the longitudinal direction from the distal end 4 of the device, the distal end 4 of the device being closed by the membrane 9 so that a soft atraumatic cushion is formed between the closed end 18' of the anchoring sleeve 15' and the closed end 4 of the device. In all of these embodiments, the support elements are inflated by the pressurized fluid that flows from the lumen 6 of the drive shaft 1 into the inflatable support elements 3, 23 only through apertures 41, 42 located proximal to the closed distal end 18' of the anchoring sleeve 15'.

FIGS. 21 to 24 illustrate third and fourth modifications of the second embodiment of the device in which the torque transmitting coil 2 does not extend under the fluid inflatable support elements 3, 23. These Figures show that the anchoring sleeve 15' lines the torque transmitting coil 2 and extends distally from a distal end 12' of the torque transmitting coil 2 such that the inflatable support elements 3, 23 are spaced away from the distal end 12' of the torque transmitting coil 2. These embodiments show that the abrasive element 5 is attached to the membrane 9 by a flexible strap 11 which extends around the membrane 9. It should be noted that the abrasive element itself may extend around the entire circumference of the membrane 9 or the anchoring sleeve 15', therefore making the strap unnecessary in this and other embodiments of the invention.

FIG. 22 illustrates best the third modification of the second embodiment of the device in which the wall 7 of the distal fluid inflatable support element 3 defines a fluid inflatable space 50' that extends only partially around a circumference of the anchoring sleeve 15' so that, when the distal inflatable support element 3 is fluid inflated, its centre of mass $CM_{DC}$ is offset from the longitudinal axis X-X of the torque transmitting coil 2 and the lumen 6 of the drive shaft 1 in one direction, the distal fluid inflated support element 3 acting, during rotation of the drive shaft 1, as a counterweight to the abrasive element 5 which has its centre of mass offset from the longitudinal axis X-X of the torque transmitting coil 2 and the lumen 6 of the drive shaft 1 in the opposite direction.

Preferably, in this third modification of the second embodiment, the device also has a proximal fluid inflatable support element 23. The wall 27 of the proximal fluid inflatable support element 23 defines a fluid inflatable space 70' that extends only partially around a circumference of the anchoring sleeve 15' so that, when the proximal inflatable support element 23 is fluid inflated, its centre of mass $CM_{PC}$ is offset from a longitudinal axis X-X of the torque transmitting coil 2 and the lumen 6 of the drive shaft 1 in one direction, the proximal fluid inflated support element 23 acting, during rotation of the drive shaft 1, as a counterweight to the abrasive element 5 which has its centre of mass offset from the longitudinal axis X-X of the torque transmitting coil 2 and the lumen 6 of the drive shaft 1 in the opposite direction.

FIG. 24 illustrates best the fourth modification of the second embodiment of the device in which a fluid inflatable space 80 within the distal fluid inflatable support element 3' extends uniformly around an entire circumference of the anchoring sleeve 15' to provide the distal support element 3' with a centre of mass which lies along the longitudinal axis X-X of the torque transmitting coil 2 and the lumen 6 of the drive shaft 1 when said distal support element 3' is fluid inflated.

Preferably, in this fourth modification of the second embodiment, the device also has a proximal fluid inflatable support element 23' in which a fluid inflatable space 100 extends uniformly around a longitudinal axis X-X of the torque transmitting coil 2 and the lumen 6 of the drive shaft 1, therefore providing the fluid inflated proximal support element 23'' with a centre of mass which lies along the longitudinal axis X-X of the torque transmitting coil 2 and the lumen 6 of the drive shaft 1 when the proximal support element 23' is fluid inflated.

FIGS. 25 and 26 illustrate a fifth modification of the second embodiment of the device. The embodiment of FIGS. 25, 26 is similar to the fourth modification of the second embodiment shown in FIG. 23, 24 but differs in that the drive shaft 1 comprises inner 102 and outer 104 torque transmitting coils. The anchoring sleeve 15' is sandwiched between the inner 102 and outer 104 torque transmitting coils. The anchoring sleeve 15' and the inner torque transmitting coil 102 extend distally from the distal end 114 of the outer torque transmitting coil 104 such that the inflatable support elements 3', 23' formed around the anchoring sleeve 15' from the fluid impermeable membrane 9 are spaced away from the distal end 114 of the outer torque transmitting coil 104. The abrasive element 5 is mounted to the drive shaft 1 between and spaced away from the support elements 3', 23', therefore locating the abrasive element 5 distal to and spaced away from the distal end 114 of the outer torque transmitting coil 104.

FIGS. 27 to 29 illustrate a sixth modification of the second embodiment of the device and its advancement across the stenotic lesion 200 to be treated. FIG. 27 shows that the rotational device of the invention has been advanced across the stenotic lesion 200 to a position in which the distal fluid inflatable support element 3 is positioned distal to the stenotic lesion 200 and the proximal fluid inflatable support element 23 is intentionally positioned proximal to the stenotic lesion 200 to be treated. The device of FIG. 27 is similar to the device of FIG. 21, but differs in that it comprises an elongate core element 300 advanceable through the long lumen 6 of the drive shaft 1 to stiffen the drive shaft 1 and thereby assist in the advancement of the device along the vessel 222 towards and across the stenotic lesion 200.

The core element 300 is shown as partially withdrawn from the lumen 6 of the drive shaft 1 in FIG. 28 and completely withdrawn in FIG. 29. It should be noted that it is necessary to completely remove the core element 300 from the long lumen 6 of the drive shaft 1 and the rest of the device to allow attachment of a detachable fluid supply tube (not shown) to the device.

FIG. 30 illustrates an antegrade flow of pressurized fluid through the device and retrograde flow of fluid around the device and across the stenotic lesion 200 to be treated. It should be noted that the pressurized fluid flowing through the device is entering the treated vessel only through the openings in the walls of the inflated support elements 3, 23.

The device of the present invention is not rotated around a guidewire. Therefore, in order to prevent damage of the wall of the treated vessel by a distal end of the device, the distal fluid inflatable support element should be inflated prior to commencing high speed rotation of the drive shaft.

FIGS. 31 to 36 illustrate abrading of the stenotic lesion 200 by the rotating abrasive element 5 and formation of layers of fluid between the walls of the rotating fluid inflated support elements 3, 23 and the inner surface of the treated vessel 222, said layers of fluid acting as fluid bearings between the walls of the rotating fluid inflated support elements 3, 23 and the wall 230 of the treated vessel 222. FIGS. 31 to 36 show that the wall 7 of the distal fluid inflatable support element 3 has an outflow opening 66 (not indicated in FIGS. 31 to 36 but indicated in previous Figures) located such that said outflow opening 66, during rotation of the drive shaft 1, faces an inner surface of a treated vessel 222 so that fluid flowing through the outflow opening 66 forms a layer of fluid between the wall 7 of the rotating fluid inflated distal support element 3 and a wall 230 of the treated vessel 222, said layer of fluid forming a fluid bearing between the wall 7 of the rotating fluid inflated distal support element 3 and the wall 230 of the treated vessel 222. FIGS. 31 to 36 also show that the wall 27 of the proximal fluid inflatable support element 23 has an outflow opening 99 (not indicated in FIGS. 31 to 36 but indicated in previous Figures) located such that said outflow opening 99, during rotation of the drive shaft 1, faces an inner surface of a treated vessel 222 so that fluid flowing through the outflow opening 99 forms a layer of fluid between the wall 27 of the rotating fluid inflated proximal support element 23 and the wall 230 of the treated vessel 222, said layer of fluid forming a fluid bearing between the wall 27 of the rotating fluid inflated proximal support element 23 and the wall 230 of the treated vessel 222.

FIG. 37 shows the distal end portion of the device after rotation of the device has been stopped but prior to stopping the flow of pressurized fluid along the lumen 6 of the drive shaft 1. Preferably, the antegrade flow FF of pressurized fluid through the device and the retrograde flow RF of fluid across the treated stenotic lesion 200 should be continued for at least a short period of time after rotation of the drive shaft 1 has been stopped so that, any embolic particles EP remaining in the treated vessel or which may still be released from the treated stenotic lesion 200 are entrained by the fluid which enters the treated vessel through the openings in the wall of the inflated distal support element 3 and flows retrograde across the treated stenotic lesion 200. Preferably, all the embolic particles EP should be removed from the treated vessel 222 and from the patient.

FIG. 38 shows the distal end portion of the device after the flow of pressurized fluid along the lumen 6 of the drive shaft 1 has been stopped. FIGS. 39 and 40 illustrate the removal of the device from the treated vessel 222 and appearance of the treated vessel 222 after removal of the device.

FIGS. 27 to 40 illustrate removal of the stenotic lesion 200 by the rotational atherectomy device with the fluid inflatable support elements 3, 23 that act, during rotation of the drive shaft, as counterweights to the eccentric or eccentrically mounted abrasive element 5. It should be noted that both modifications of the rotational atherectomy device with concentric (symmetric) fluid inflatable support elements 3', 23' shown in FIGS. 23 to 26 may be equally effective or even preferred for removing stenotic lesions in the carotid arteries. FIGS. 23 to 26 show that the abrasive element 5 is eccentrically mounted between the concentric fluid inflatable support elements 3', 23'. The concentric fluid inflatable support elements 3', 23' of such device usually have the fluid inflatable spaces 80, 100 that extend uniformly around the longitudinal axis X-X of the torque transmitting coil 2 and the lumen 6 of the drive shaft 1. Therefore, the walls 7, 27 of the fluid inflatable concentric (symmetric) support elements 3', 23' should have at least a few openings 66, 99 equally spaced from each other around circumferences of the walls 7, 27 of the support elements 3', 23' such that at any time during rotation of the drive shaft 1 at least one opening within each group of said openings 66, 99 is facing an inner surface of a treated vessel, so that a flow of fluid through the openings 66, 99 forms a layer of fluid between the walls 7, 27 of the rotating fluid inflated support elements 3', 23' and a wall of the treated vessel, said layer of fluid forming a fluid bearing between the walls 7, 27 of the rotating fluid inflated support elements 3', 23' and the wall of the treated vessel.

It should be also noted that the rotational atherectomy device with concentric (symmetric) fluid inflatable support elements and concentric (symmetric) abrasive element may be useful or even preferred for removing stenotic lesions in the curved arteries. The symmetric distal and proximal fluid inflatable support elements of such device should both have at least a few openings equally spaced from each other around circumference of the wall of the support element such that at any time during rotation of the drive shaft at least one of each of the two sets of openings is facing an inner surface of a treated vessel, so that a flow of fluid through the openings forms a layer of fluid between the wall of the rotating fluid inflated support element and a wall of the treated vessel, said layer of fluid forming a fluid bearing between the wall of the rotating fluid inflated support element and the wall of the treated vessel.

Figure 41:
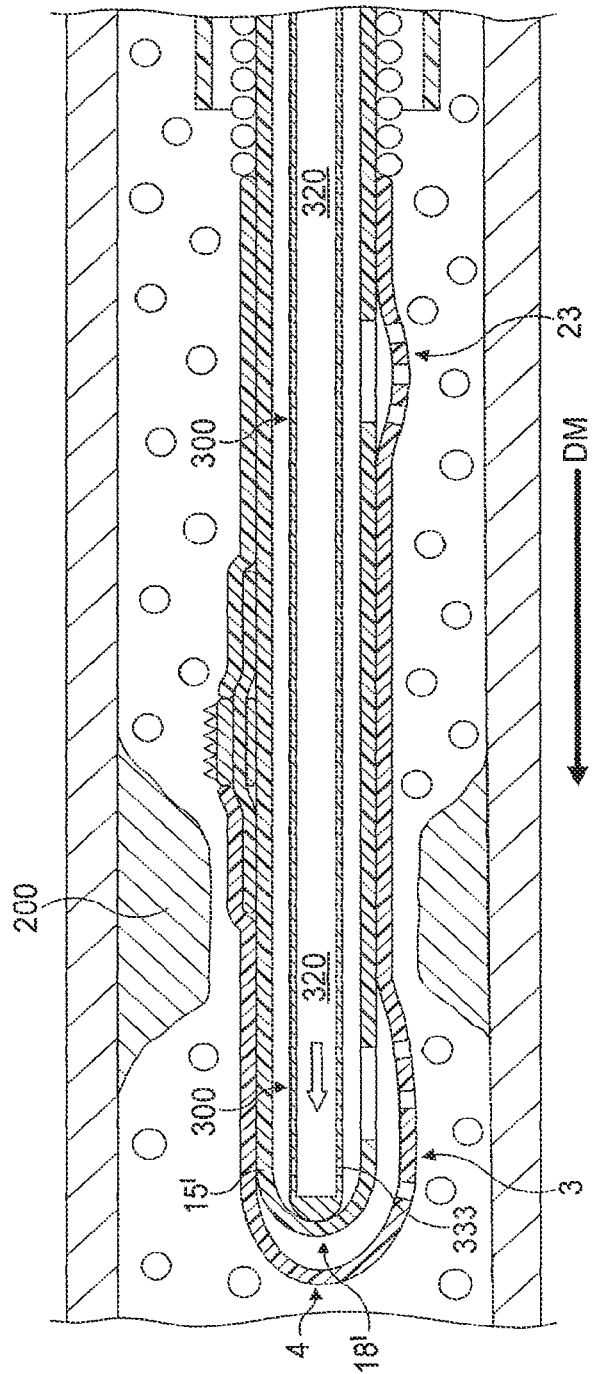
FIG. 41 shows a seventh modification of the second embodiment of the device of the invention. The device shown

FIG. 41 shows yet another modification of the third embodiment of the device. The embodiment of FIG. 41 is similar to the embodiment of FIG. 27 except that the core element 300'shown in FIG. 41 comprises a long lumen 330 configured for transferring pressurized fluid into the lumen 6 of the drive shaft through an opening 333 located in a wall of the (hollow) core element 300'. The opening(s) 333 are located adjacent to a distal end 337 of the (hollow) core element 300'. FIG. 42 shows the device of FIG. 41 in which pressurized fluid is flowing from the lumen 330 of the core element 300' into the lumen 6 of the drive shaft 1 such that a layer of fluid is formed between the wall of the core element 300' and the wall of the drive shaft 1 of the rotational atherectomy device. FIG. 43 shows the device of FIG. 42 in which the core element 300' is being withdrawn from the lumen 6 of the drive shaft 1 and the device. It should be noted that continuous flow of the pressurized fluid from the lumen of the core element 300' into the lumen 6 of the drive shaft 1 is reducing friction between the core element 300'and the wall of the lumen 6 of the drive shaft 1 and thereby is assisting in removing the core element from the device without changing position of the device in the treated vessel.

FIG. 44 shows the device of FIG. 42 after flow of pressurized fluid has been initiated through the lumen 320 of the core element 300' and the rest of the device at a fluid flow rate which is sufficient to inflate the distal support element 3 and anchor it distal to the stenotic lesion 200. FIG. 45 illustrates how the anchoring of the inflated distal support element 3 against the stenotic lesion 200 is assisting in removing the core element 300' from the lumen 6 of the drive shaft 1 without changing the position of the rest of the device in the treated vessel. It should be noted that the stiffening of the drive shaft 1 by the pressure of the fluid on the wall of the lumen 6 of the drive shaft 1 is also assisting in the removal of the core element 300' from the drive shaft 1 without changing the position of the rest of the device in the treated vessel.

FIGS. 46 and 47 illustrate the fourth embodiment of the device in which the wall 7" of the distal fluid inflatable support element 3" is made from a fluid impermeable stretchable membrane 9". The stretchable membrane 9" proximal to the distal fluid inflatable support element 3" is sandwiched between the torque transmitting coil 2 of the drive shaft 1 and a non-stretchable sleeve 500. Preferably, the fluid impermeable stretchable membrane 9" extends around the torque transmitting coil 2 in proximal direction to form the wall 27" of the proximal fluid inflatable support element 23". The non-stretchable sleeve 500 may extend around the stretchable membrane uninterrupted between the distal and proximal fluid inflatable support elements as shown in FIGS. 46 it may be divided in two sections 510, 520 as shown in FIGS. 47 and 48. FIGS. 47 and 48 show that the sections 510, 520 of the non-stretchable sleeve 500 are disposed on either side of the abrasive element 5. FIGS. 46 to 48 also show a second long, non-stretchable sleeve 600 which overlaps the stretchable membrane 9"for a short distance proximal to the proximal fluid inflatable support element 23" and extends in a proximal direction around the torque transmitting coil 2 towards the proximal end of the drive shaft 1.

It should be noted that the fluid inflatable support elements may be formed either from stretchable fluid impermeable sleeves or from non-stretchable sleeves which have a larger diameter in the areas of the fluid inflatable support elements and which are simply furled around the drive shaft when drive shaft is advanced to, and across, the lesion to be treated.

Figure 49:
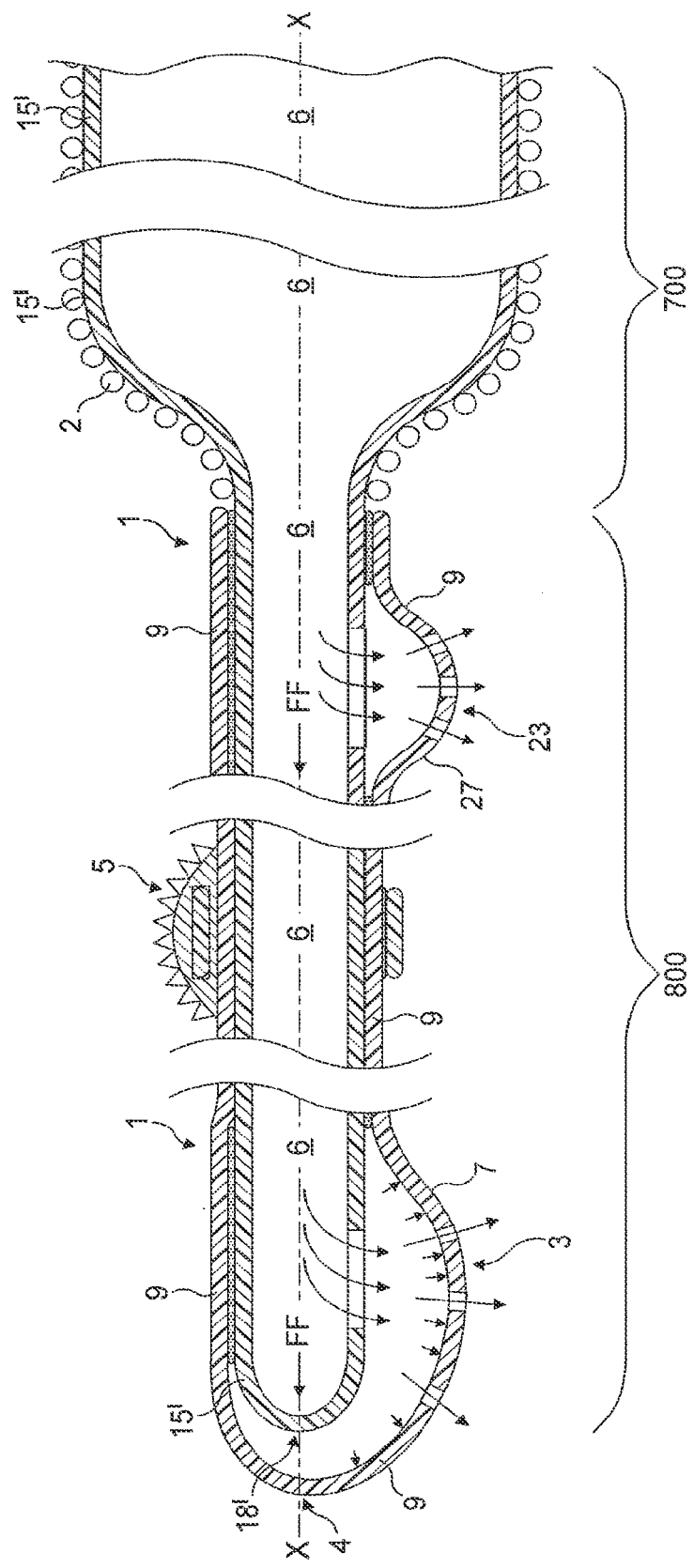
FIG. 49 illustrates a fourth embodiment of the device.

FIG. 49 illustrates the fifth embodiment of the device. The embodiment of FIG. 50 is similar to the embodiment of FIG. 27 except that the lumen 6' of the drive shaft 1 includes proximal and distal portions having different cross-sectional areas. The proximal portion 700 of the the lumen 6' has a larger cross-sectional area relative to the cross-sectional area of the distal portion 800 of the lumen 6' so that, per unit of length, hydraulic resistance to fluid flow of the proximal portion 700 of the lumen 6' is less than the hydraulic resistance to fluid flow of the distal portion 800 of the lumen 6'.

It should be noted that the fluid inflatable support elements 3, 23 of the fifth embodiment shown in FIG. 49 are illustrated as being formed from a non-stretchable membrane. The non-stretchable walls 7, 27 of the fluid inflatable support elements 3, 23 should be simply furled around the drive shaft when the device is advanced to, and across, the stenotic lesion to be treated.

It should be also noted that the fluid inflatable support elements shown in FIG. 49 and in any of FIGS. 1 to 45 may be formed from a stretchable membrane.

The invention claimed is:

1. A system for performing rotational atherectomy to remove stenotic lesion material from a blood vessel of a patient, the system comprising:
    an elongate drive shaft sheath defining a sheath lumen therethrough, the drive shaft sheath being configured to be at least partially disposed within the blood vessel; and
    a rotational atherectomy device slidable through the elongate drive shaft sheath toward stenotic lesion material in a blood vessel, comprising:
        an elongate flexible drive shaft defining a central lumen and a longitudinal axis, the drive shaft configured for rotation about the longitudinal axis, the drive shaft including a proximal region that is configured to be at least partially disposed within the sheath lumen when the drive shaft is rotated for performing rotational atherectomy;
        an abrasive element that is fixed to the drive shaft such that a center of mass of the abrasive element is offset from the longitudinal axis of the drive shaft;
        a distal stability element that is coupled with the drive shaft and that has a center of mass aligned with the longitudinal axis of the drive shaft, the distal stability element being distally spaced apart from the abrasive element by a distal separation distance; and
        a fluid impermeable layer along the drive shaft and surrounding an outer diameter of the drive shaft between the abrasive element and the distal stability element and to at least one exit port located at a distal end of the rotational atherectomy device,
        wherein the distal separation distance is less than a distance between the abrasive element and a distal end of the rotational atherectomy device.

2. The system of claim 1, further comprising a proximal stability element that is coupled with the drive shaft and that has a center of mass aligned with the longitudinal axis of the drive shaft, the proximal stability element being proximally spaced apart from the abrasive element by a proximal separation distance, wherein the proximal stability element comprises an inflatable stability element.

3. The system of claim 2, wherein the fluid impermeable layer surrounds the outer diameter of the drive shaft at least between the proximal stability element and the distal stability element.

4. The system of claim 1, wherein the distal stability element comprises an inflatable stability element.

5. The system of claim 1, wherein an outer diameter of the abrasive element is greater than an outer diameter of the distal stability element.

* * * * *